(12) United States Patent
Coopersmith et al.

(10) Patent No.: US 12,127,910 B2
(45) Date of Patent: Oct. 29, 2024

(54) ANIMAL DENTAL HYGIENIC DEVICE

(71) Applicants: Allan Coopersmith, Westmount (CA);
Nathalie Fiset, Westmount (CA)

(72) Inventors: Allan Coopersmith, Westmount (CA);
Nathalie Fiset, Westmount (CA)

( * ) Notice: Subject to any disclaimer, the term of this patent is extended or adjusted under 35 U.S.C. 154(b) by 0 days.

(21) Appl. No.: 15/967,624

(22) Filed: May 1, 2018

(65) Prior Publication Data
US 2018/0243063 A1   Aug. 30, 2018

Related U.S. Application Data

(63) Continuation of application No. PCT/IB2017/057472, filed on Nov. 28, 2017.
(Continued)

(51) Int. Cl.
*A61D 5/00*    (2006.01)
*A01K 13/00*   (2006.01)
(Continued)

(52) U.S. Cl.
CPC .............. *A61D 5/00* (2013.01); *A01K 13/001* (2013.01); *A01K 15/026* (2013.01);
(Continued)

(58) Field of Classification Search
CPC .......... A61D 5/00; A61D 7/00; A01K 15/026; A46B 11/0041; A46B 11/0065;
(Continued)

(56) References Cited

U.S. PATENT DOCUMENTS

| 4,802,444 A | 2/1989 | Markham et al. |
| 5,033,410 A | 7/1991 | Sigurdsson |

(Continued)

FOREIGN PATENT DOCUMENTS

| EP | 0526667 | 2/1993 |
| EP | 2735227 A1 | 5/2014 |

(Continued)

OTHER PUBLICATIONS

International Search Report from PCT/IB2017/057472, Feb. 19, 2018, Alexis Cote.
(Continued)

*Primary Examiner* — Jacqueline T Johanas
*Assistant Examiner* — Drew S Folgmann
(74) *Attorney, Agent, or Firm* — FASKEN MARTINEAU DUMOULIN LLP; Dennis Haszko

(57) ABSTRACT

Animal dental hygienic device, comprising: A hollow body having an exterior surface and an interior cavity, and being sized to fit within the mouth of the animal and to be bitten thereby. The hollow body having a plurality of apertures positioned along its exterior surface, the apertures extending from the exterior surface to the interior cavity. Each aperture having dental-hygienically active dimensions allowing an animal's tooth to penetrate through the aperture; such that (i) material surrounding the aperture frictionally engages the animal's tooth's outer surface during penetration of the aperture by the tooth, the material surrounding the aperture being of sufficient hardness to scrape the tooth's outer surface during frictional engagement to remove dental plaque, and (ii) a portion of the animal's tooth extends within the interior cavity during penetration of the aperture by the tooth.

5 Claims, 46 Drawing Sheets

Related U.S. Application Data

(60) Provisional application No. 62/571,689, filed on Oct. 12, 2017, provisional application No. 62/467,431, filed on Mar. 6, 2017, provisional application No. 62/497,616, filed on Nov. 28, 2016.

(51) Int. Cl.
| | | |
|---|---|---|
| *A01K 15/02* | (2006.01) | |
| *A46B 9/00* | (2006.01) | |
| *A46B 11/00* | (2006.01) | |
| *A61C 17/02* | (2006.01) | |
| *A61D 7/00* | (2006.01) | |
| *A61K 8/02* | (2006.01) | |
| *A61K 8/97* | (2017.01) | |
| *A61Q 11/00* | (2006.01) | |

(52) U.S. Cl.
CPC ...... *A46B 11/0041* (2013.01); *A46B 11/0065* (2013.01); *A61D 7/00* (2013.01); *A61K 8/0233* (2013.01); *A61K 8/97* (2013.01); *A61Q 11/00* (2013.01); *A46B 9/005* (2013.01); *A46B 2200/1066* (2013.01); *A46B 2200/1086* (2013.01); *A46B 2200/1093* (2013.01); *A61C 17/0211* (2013.01)

(58) Field of Classification Search
CPC ............ A46B 9/005; A46B 2200/1066; A46B 2200/1086; A46B 2200/1093; A61K 8/0233; A61K 8/97; A61Q 11/00; A61C 17/0211
See application file for complete search history.

(56) References Cited

U.S. PATENT DOCUMENTS

| | | | |
|---|---|---|---|
| 5,126,137 A | 6/1992 | Ambert | |
| RE34,352 E * | 8/1993 | Markham | A61D 5/00 119/710 |
| 5,427,120 A * | 6/1995 | Wong | A45D 19/02 132/120 |
| 5,647,302 A * | 7/1997 | Shipp | A01K 15/026 119/709 |
| 5,865,146 A | 2/1999 | Markham | |
| 5,921,255 A | 7/1999 | Garita | |
| 5,944,516 A * | 8/1999 | Deshaies | A61D 5/00 15/167.1 |
| D431,886 S | 10/2000 | Owens | |
| D432,741 S | 10/2000 | Owens | |
| D433,778 S | 11/2000 | Axelrod | |
| 6,148,771 A | 11/2000 | Costello | |
| 6,202,598 B1 | 3/2001 | Willinger | |
| 6,305,326 B1 | 10/2001 | Suchowski | |
| 6,405,681 B1 | 6/2002 | Ward | |
| 6,439,166 B1 | 8/2002 | Markham | |
| 7,490,579 B2 | 2/2009 | Axelrod | |
| 7,789,045 B1 | 9/2010 | Tsengas | |
| D659,296 S | 5/2012 | Andserson | |
| 8,875,662 B2 * | 11/2014 | Angle | A01K 15/026 119/707 |
| D725,866 S | 4/2015 | Barnvos | |
| D751,266 S | 3/2016 | Donatucci | |
| D752,841 S | 4/2016 | Neely | |
| D759,341 S | 6/2016 | Templeman | |
| 9,661,830 B2 | 5/2017 | Barnvos | |
| 9,737,053 B2 | 8/2017 | Barnvos | |
| D801,620 S | 11/2017 | Falcone | |
| 9,844,207 B1 | 12/2017 | Wright et al. | |
| D809,219 S | 1/2018 | Wright et al. | |
| D812,340 S | 3/2018 | Falcone | |
| D815,780 S | 4/2018 | Pater | |
| D817,561 S | 5/2018 | Pater | |
| D822,940 S | 7/2018 | Falcone | |
| D825,116 S | 8/2018 | Wills | |
| 10,285,380 B1 | 5/2019 | Mullin | |
| 10,448,615 B1 | 10/2019 | Mullin | |
| D869,105 S | 12/2019 | Bao | |
| 10,602,720 B1 | 3/2020 | Schwartz | |
| 10,772,298 B1 | 9/2020 | Mullin | |
| 11,224,203 B2 | 1/2022 | Spivak | |
| 2004/0137118 A1 | 7/2004 | Alexrod | |
| 2004/0215234 A1 | 10/2004 | McCardell | |
| 2004/0216693 A1 | 11/2004 | Handelsman | |
| 2005/0166865 A1 | 8/2005 | Handelsman | |
| 2006/0102099 A1 | 5/2006 | Edwards | |
| 2006/0107905 A1 | 5/2006 | Alexrod | |
| 2006/0150919 A1 | 7/2006 | Thomason | |
| 2006/0201446 A1 * | 9/2006 | Edwards | A01K 15/026 119/707 |
| 2007/0006818 A1 | 1/2007 | Bidinger | |
| 2007/0015100 A1 * | 1/2007 | Morris | A61D 5/00 433/1 |
| 2008/0041320 A1 | 2/2008 | Torney | |
| 2009/0038559 A1 | 2/2009 | Markham | |
| 2009/0038560 A1 | 2/2009 | Markham | |
| 2009/0114166 A1 | 5/2009 | Saborio et al. | |
| 2009/0151649 A1 | 6/2009 | Vardy et al. | |
| 2010/0003393 A1 | 1/2010 | Torney | |
| 2010/0136162 A1 | 6/2010 | Cupp | |
| 2010/0147228 A1 | 6/2010 | Lind | |
| 2011/0011351 A1 | 1/2011 | Simoni | |
| 2011/0214617 A1 | 9/2011 | Markham | |
| 2011/0259282 A1 | 10/2011 | Tsengas | |
| 2012/0111284 A1 | 5/2012 | Berger | |
| 2012/0279459 A1 | 11/2012 | Angle | |
| 2013/0036988 A1 | 2/2013 | Lai | |
| 2013/0251872 A1 | 9/2013 | Axelrod | |
| 2013/0266905 A1 * | 10/2013 | Smith | A01K 15/026 433/1 |
| 2014/0045135 A1 * | 2/2014 | Beckman | A46B 9/005 433/1 |
| 2019/0167979 A1 | 6/2019 | Ruflin | |
| 2019/0208939 A1 | 7/2019 | Jeuberger | |
| 2019/0274279 A1 | 9/2019 | Hayashi | |

FOREIGN PATENT DOCUMENTS

| | | |
|---|---|---|
| GB | 2413503 A | 11/2005 |
| JP | 2002262697 A | 9/2002 |
| WO | 8000379 | 1/1989 |
| WO | 2004062358 A1 | 7/2004 |
| WO | 2005072519 A1 | 8/2005 |
| WO | 2009039153 A1 | 3/2009 |

OTHER PUBLICATIONS

JP2002262697A—Printout from Google Patents on Mar. 2, 2022.
WO2004062358A1—Printout from Google Patents on Mar. 2, 2022.
WO2005072519A1—Printout from Google Patents on Mar. 2, 2022.

* cited by examiner

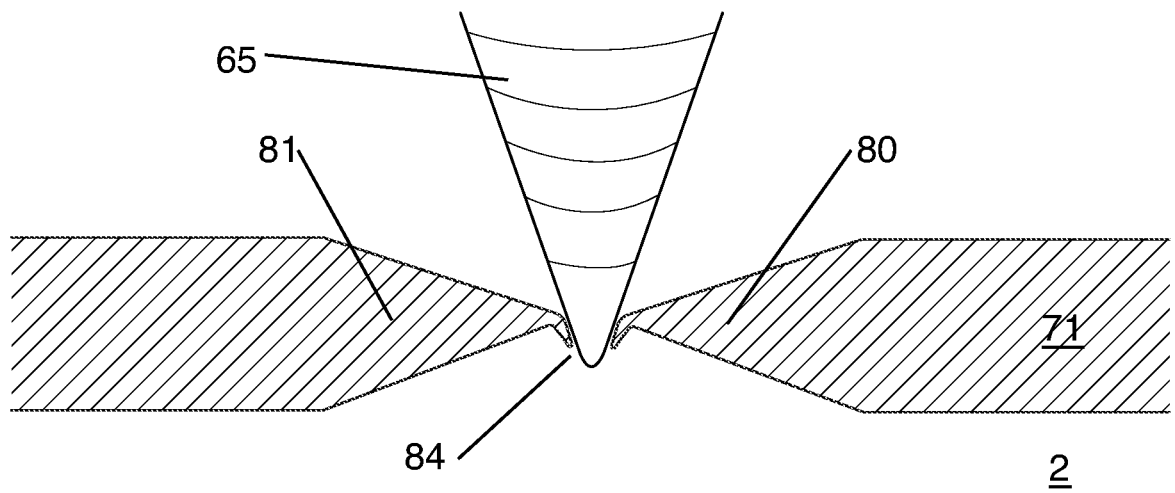
Figure 17bis
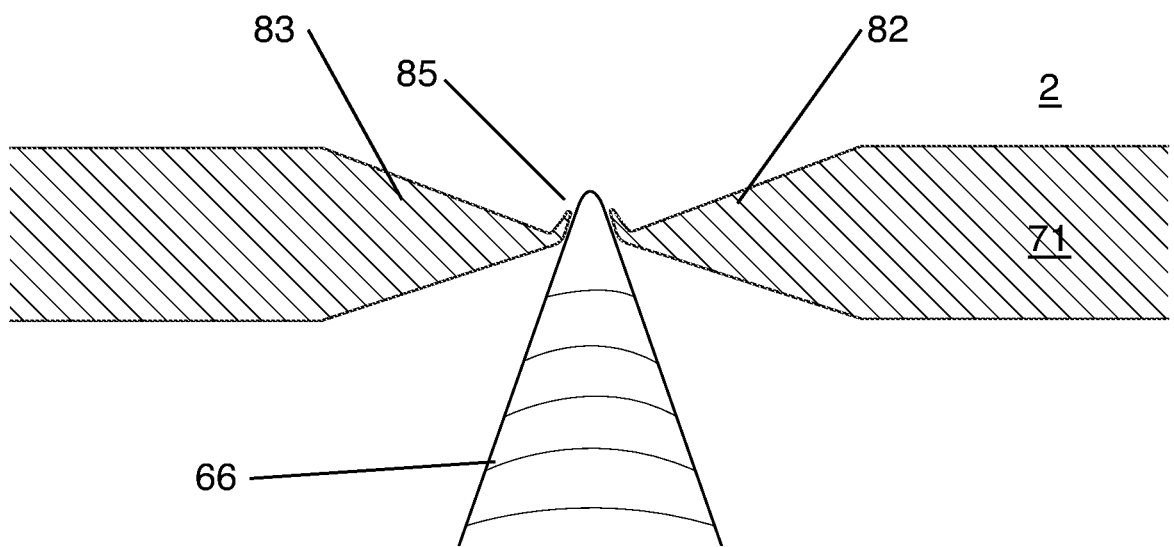
Figure 18bis

ANIMAL DENTAL HYGIENIC DEVICE

CROSS-REFERENCE

The present application is a continuation of International Patent Application No. PCT/IB2017/057472, filed Nov. 28, 2017, entitled "Animal Dental Hygienic Device". Via the '472 International Application: (1) The present application claims priority to U.S. Provisional Patent Application No. 62/497,616, filed Nov. 28, 2016, entitled "Dental Cleaning Application Device and Method". (2) The present application also claims priority to U.S. Provisional Patent Application No. 62/467,431, filed Mar. 6, 2017, entitled "Dental Cleaning and Application Device and Method". (3) The present application also claims priority to U.S. Provisional Patent Application No. 62/571,689, filed Oct. 12, 2017, entitled "Animal Dental Hygienic Device". The entire contents of all of the foregoing patent applications are incorporated herein by reference.

FIELD

The present technology relates to dental hygienic devices for animals (including humans).

BACKGROUND

Domesticated animals, such as cats and dogs, often need dental care to prevent dental problems commonly due to plaque, tartar, tooth decay, gingivitis, periodontal disease, and the like. Poor dental health in such animals is, unfortunately, very common. Indeed, periodontal disease is one of the most frequently treated diseases by veterinarians in the United States.

Most periodontal disease starts with the formation of a film of a soft amorphous biofilm called plaque, consisting primarily of oral bacteria, bacterial by-products, and oral debris. This film typically covers both the exposed tooth surface and the area lying under the gum line, the gingival cavity (sulcus). Through the deposition of calcium and other mineral salts, this layer of plaque hardens and develops into tartar. Although tartar is hard, it is also porous and adheres to the tooth surface. Tartar appears to be progressively deposited in layers and provides a rough surface onto which more plaque is deposited. As tartar builds up, a broad range of microbes can attach. The by-products of metabolism from these bacteria cause inflammation of local tissues including those surrounding the gingival cavity. This ultimately leads to periodontal disease. The earliest stage is gingivitis, characterized by inflammation of the gums. As periodontal disease progresses, gingivitis becomes periodontitis, with inflammation extending into the connective tissues surrounding the tooth. Through gingivitis and periodontitis, it is thought that harmful bacteria enter into the blood stream and ultimately lodge in the heart and other internal organs.

The long-term impact of poor dental health can be devastating. Poor dental health is thought to be a contributing factor in the deaths of dogs, cats, and other mammals. In animals, as is the case in humans, poor dental health has been linked with serious diseases of the heart, liver, kidney, and other internal organs. Indeed, one study demonstrated that every dog with periodontal disease had pathological changes in the heart, liver, and kidneys.

Dental care for animals is generally more difficult to manage than dental care for humans; animals do not voluntarily engage in tooth brushing.

Some veterinarians recommend regularly brushing the animal's teeth, but as any pet owner knows, such a task is extremely difficult. It is often difficult for the owner to keep the animal's mouth open during brushing, and the process may be extremely unpleasant for the animal and even potentially dangerous to the owner. Few animal owners are willing and able to maintain this level of home care.

Another solution is to bring the animal to the veterinarian to have it sedated and have the veterinarian perform dental care on the animal while it is under sedation. This solution, however, is not something that can reasonably be performed daily, weekly or even monthly. Sedation can be potentially harmful to the animal, especially if the animal is older.

Many domestic animal dental hygienic devices have been created in the past. Unfortunately, none to date that provide satisfactory dental cleaning for animals are found in widespread contemporary use.

As a simple example, U.S. Pat. No. 6,405,681, issued Jun. 18, 2002 to Ward, entitled "Chew Toy" provides: "An animal chew toy and a system are disclosed that are capable of dispensing a liquid, such as a dentifrice, to the oral cavity of an animal. The toy may comprise one of various shapes such as a ball or a bone shape. The chew toy may provide a reservoir containing a plurality of apertures that dispense the liquid when compressed. The reservoir may provide bristles to brush the animal's teeth during play. The liquid may be a solution that improves dental hygiene, such as fluoride, or in some instances, the solution may promote general health in the animal." [Abstract Ward].

Improvements in this area are therefore desirable.

SUMMARY

It is thus an object of the present technology to ameliorate at least some of the inconveniences present in the prior art.

It is also an object of the present technology to provide an improved animal dental hygienic device at least as compared with some of the prior art devices.

The creator of the present technology has realized several facts that are believed to be helpful in designing improved animal dental hygienic devices.

In this respect, the sides of the teeth facing the cheeks, i.e., the buccal (facial) side—located in the buccal cavity, have a greater incidence of gingivitis and plaque/tartar build-up than the sides of the teeth facing the tongue, i.e., the lingual (oral) side. It has also been found that the rear teeth, i.e., the pre-molars and molars; more rapidly develop plaque and tartar than the front teeth. Yet, typical conventional animal hygienic devices seemingly have limited efficacy in cleaning the molars and pre-molars, and this notwithstanding the fact that these are the teeth where tartar build up typically is heaviest. These teeth are also the most difficult teeth for an animal owner to clean with a toothbrush. They are thus the areas where plaque accumulation can rapidly develop into gingivitis and pathogenic bacteria enter the blood stream with potentially harmful consequences. But, if an animal dental hygienic device is poorly designed, then, during chewing, little of the device will actually enter the rear buccal cavity, thus leading to reduced abrasive action and limited cleaning of the tooth surface.

Further, typical conventional domestic animal hygienic products do not always clean the crevices of the animal's teeth, and many such products are ineffective in cleaning the areas underneath the animal's gums.

A further drawback of typical conventional animal hygienic products is that many of these products are ineffective in removing existing tartar from the teeth. Because tartar is so hard, attempting to remove tartar by the simple abrading action caused by chewing may not be effective in reducing the tartar.

A common failure of the typical conventional animal dental hygienic devices is that they are not designed to take into account the bite force exerted by the teeth and the biting behavior of the target animals. If the bite resistance is too high, then the teeth will not evenly penetrate the product and there will be little opportunity for the product to push against the gums and clean in critical areas. Conversely, if the bite resistance is too low then the animal will rapidly bite through and potentially destroy the product; thus, little pressure will be exerted against the tooth surface under the gums again leading to poor cleaning in critical areas.

Another issue is that typical conventional animal dental hygienic devices rely solely on bristles, which do not adequately clean the teeth of the animal.

Some such typical conventional animal hygienic products have oral care additives that are designed to inhibit the formation of tartar. A problem with some of these products is that they do not necessarily function as desired. In this regard, the efficacy of these agents disappears when the product is swallowed or other food is eaten by the animal. In a similar vein, some of these products are unstable and their texture changes with time, losing their cleansing properties.

The present technology was created with the foregoing information in mind. Thus, in one aspect, embodiments of the present technology provide an animal dental hygienic device, comprising: A hollow body having an exterior surface and an interior cavity. The hollow body is sized to fit within the mouth of the animal and to be bitten by the animal. The hollow body has a plurality of apertures positioned along the exterior surface of the hollow body. The apertures extend from the exterior surface to the interior cavity. Each aperture has dental-hygienically active dimensions allowing a tooth of the animal to penetrate through the aperture, such that (i) material surrounding the aperture frictionally engages an outer surface of the tooth of the animal during penetration of the aperture by the tooth, the material surrounding the aperture being of sufficient hardness (and in some embodiments also of sufficient roughness) to scrape the outer surface of the tooth during frictional engagement to remove dental plaque, and (ii) a portion of the tooth of the animal extends within the interior cavity during penetration of the aperture by the tooth.

An animal dental hygienic device of the present technology attempts to overcome at least some of aforementioned difficulties with typical conventional domestic animal dental hygienic device. As an animal chews on an appropriately sized device, the teeth of the animal will penetrate through the body of the device via the apertures (which may also be described as channels through the hollow body). During such penetration, plaque, tartar and debris are cleaned from the animal's teeth surface via being scraped against the material surrounding the apertures. The more force that the animal exerts while biting the device, the deeper that their teeth will penetrate, thus cleaning the tooth closer to the animal's gum line and potentially cleaning the gingival cavity itself.

Being designed in this manner, it is not necessary to design the material forming the hollow body to itself be penetrable by the teeth of the animal (although it may be in some embodiments). The apertures permit penetration and are appropriately sized to scrape a tooth of the animal as it penetrates therethrough. Indeed, the material surrounding the apertures (which is in many embodiments the same as the material of the remainder of the hollow body, although this is not required and is not the case in some embodiments), and the apertures themselves, may be designed and structured taking into account the typical animal's biting force in respect of which the device has been designed. In this manner, typical penetration depth of the teeth may be able to be controlled.

The hollow body may be constructed from any suitable material or combination of materials sufficient to achieve the design objective referred to hereinabove. For example, in some embodiments, the hollow body may be constructed of a single material, such as any suitable biocompatible natural or synthetic rubber or plastic. In other embodiments, the hollow body may be constructed of more than one material, such as any combination of suitable such rubbers and/or plastics. In some embodiments, all of the materials of the hollow body (be there a single material or multiple materials) are edible by the animal. (In some such embodiments, the remainder of components of the device are edible as well so that the entire device may be consumed by the animal.)

In some embodiments, the hollow body is of a single layer construction. In some embodiments, the hollow body is of a multiple layer construction with at least one of the layers being dental-hygienically active. In such embodiments, the other layers may also be dental-hygienically active and/or may serve other purposes (including structural). As non-limiting examples, a device may have a fluoride release layer, an abrasive layer, a layer that acts like a squeegee, etc. or combination thereof, or of layers serving other purposes.

In some embodiments, the hollow body is flexible while being chewed by the animal. In other embodiments, the hollow body is rigid while being chewed by the animal. It is not necessary that all portions of the hollow body have the same flexibility and/or rigidity. In some embodiments, the flexibility and/or rigidity of different portions of the hollow body varies.

In still other embodiments, the material or materials (as the case may be) of which the hollow body is constructed may have other materials added therein and/or thereon to provide the device with additional functionalities, be they dental-hygienically active or otherwise. As an example, in some embodiments a mesh may be provided within or over the material of which the hollow body is constructed for structural stability purposes. In other embodiments, other materials such as plastic or metal fibers serve a similar purpose. As another example, in some embodiments, a mesh may also be provided on the exterior surface to enhance the scraping, and thus cleaning ability, of the device.

Such suitable additional materials are not limited to those determined solely based on mechanical properties. In some embodiments, a chemical substance (material) having suitable chemical properties is associated with the hollow body. This includes chemical substances that are on the exterior surface and those that are within the material(s) of which the hollow body is constructed. This includes those chemical substances which are adhered to the surface or other part of the hollow body, which are absorbed within one or more of the materials of which the hollow body is constructed, and/or those which are adsorbed to one or more of the materials of which the hollow body is constructed. This includes materials of which the hollow body is constructed that release chemical substances as a result of the chewing and/or biting action of the animal on the device. This includes chemical substances that result from the breakdown of other materials or substances when in contact with a liquid such as water and/or the saliva of the animal. Such chemical substances may be a single chemical substance or a combination of chemical substances. Such chemical substances may have one or more desired functionalities. For example, such a chemical substance may be an anti-bacterial (be it to attempt to reduce the number of bacteria growing in or on the device or otherwise). Such a chemical substance may be a medicament (be it a dental medicament to assist in dental hygiene (e.g., fluorine, a dental disinfectant, etc.) or a medicament for some other purpose such as an antibiotic or medicine intended to be ingested by the animal for action in another part of the animal's body other than the mouth). Such a chemical substance may be a fragrance (be it one intended to attract the animal to the device and/or one intended to reduce or eliminate any malodorousness of the device and/or one intended to render the device (or its environment) more aromatic). Such chemical substance may be a flavor, such as one intended to make the device more attractive to the animal. Such a chemical substance may be a nutrient, such as a vitamin, a mineral, or a combination thereof. Such a chemical substance may also be mechanical, such as an abrasive, which may add in cleansing the tooth of the animal.

The apertures may be of any shape sufficient to accomplish their intended function as described hereinabove. For example, in different embodiments, the apertures will be of one or more of the following shapes: slits, crosses, zigzags, stars, etc. (This list is not intended to be limiting, merely exemplary.) In some embodiments, all of the apertures of the device are of the same shape; but this is not required to always be the case. In some embodiments, different apertures of the same device have different shapes.

Further the apertures may be of any thickness sufficient to allow a tooth of an animal (for which the device is designed) penetrating the aperture to extend into the internal cavity of the hollow body, as will be further described hereinbelow.

In some embodiments, the apertures further have structures therein that assist in their scraping function. Non-limiting examples include edges that are beveled, honeycomb-like projections, etc.

In some embodiments, the hollow body is constructed of material having sufficient flexibility to deform under pressure exerted by the animal biting the hollow body, and the dimensions of apertures change during deformation from initial dimensions to the dental-hygienically active dimensions. Dental-hygienically active dimensions are those sufficient to accomplish the function of the apertures as was previously described. In some such embodiments, the initial dimensions are themselves dental-hygienically active dimensions. In some other such embodiments, the initial dimensions are themselves not dental-hygienically active dimensions. As an example, in some such embodiments, the apertures are slits in which the side walls touch each other (effectively closing the apertures) until pressure from the animal's biting the hollow body causes a deformation which separates the side walls form one another, opening the apertures.

In some embodiments, at least some apertures are at least partially closed by at least one frangible closure broken open by the tooth of the animal penetrating the closure. In some embodiments, at least some apertures are only partially formed in the hollow body as manufactured (prior to being the device being bitten by the animal) (e.g., apertures that upon manufacturing extend from the exterior surface into the hollow body but not completely to the interior cavity; apertures that extend from the interior cavity into the hollow body but not completely to the exterior surface; apertures that extend within the hollow body towards both the exterior surface and the interior cavity but that communicate with neither). In such embodiments, the apertures are caused to extend from the exterior surface to the interior cavity as the animal bites the device (e.g., by tearing, ripping and/or piercing).

In some embodiments, at least some of the material or materials (as the case may be) of which the hollow body is constructed may have a cancellous structure defining a network of small cell-like cavities; such cell-like cavities having a certain shape, a certain average size and a certain average density. In such embodiments, it is not necessary that all portions of the hollow body having such a cancellous structure have the same shape, average size and/or density of cell-like cavities. In some such embodiments, the shape and/or average size and/or density of cell-like cavities of different portions of the hollow body vary. In some such embodiments, apertures are defined by at least some of the cell-like cavities of the hollow body that are interconnected. In some such embodiments, apertures are defined by at least some of the cell-like cavities of the hollow body that are interconnectable upon the animal biting the device. In some such embodiments, the internal cavity is defined by the largest cell-like cavity of the hollow body.

In some embodiments, projections extend outwardly from the exterior surface of the hollow body, the projections being positioned, dimensioned, shaped and structured to be dental-hygienically active as the animal bites the hollow body. In the context of the present technology no particular projection position, dimension, shape or structure is required as long as the function of dental-hygienically activeness is met. Non-limiting examples of projection shapes are cylinders, rods, honeycomb-like, plates, etc.

The projections may be of the same material as the hollow body or of a different material. Non-limiting examples of projection materials include plastic, silicone, wood, and edible substances.

In some embodiments, the dental-hygienically activeness of the projections occurs as the projections frictionally engage at least the outer surface of the tooth of the animal as the tooth penetrates an aperture, thus removing plaque and/or tartar from the outer surface of the tooth. In some embodiments, the dental-hygienically activeness of the projections occurs as the projections frictionally engage at least the gums of the animal as the tooth of the animal penetrates an aperture. In some such embodiments, the projections assist in cleaning the gingival cavity of the tooth of the animal.

In some such embodiments, when the material of which the hollow body is constructed deforms under pressure, for example as was described hereinabove, the projections move from an initial configuration to a dental-hygienically active configuration. Dental-hygienically active configurations are those sufficient to provide a dental function to the projections, for example as were previously described. In some such embodiments, the initial dimensions are themselves dental-hygienically active dimensions. In some other such embodiments, the initial dimensions are themselves not dental-hygienically active dimensions. Both cases are within the scope of the present technology. The projections may have one or more chemical substances associated with them as was described hereinabove in relation to the hollow body itself.

As was stated hereinabove, each aperture is dimensioned such that a portion of the tooth of the animal extends within the interior cavity during penetration of the aperture by the tooth when the animal chews and/or bites the device. In many embodiments, a filler material is present within the interior cavity of the device. In some such embodiments, the filler material completely fills the interior cavity. In most of some such embodiments, the filler is a material (or materials) different than material(s) of which the hollow body is constructed.

The range of filler materials within the scope of the present technology is vast. Non-limiting examples include the following: In some embodiments, for example in those wherein the hygienic device that is intended for use by dogs, the filler material may contain wood. As dogs like to chew wooden sticks, having a filler in the form of a wooden stick may induce dogs to chew the device for relatively longer periods of time, providing a better cleaning of their teeth. For similar reasons, in some embodiments, the filler material may contain rawhide. In other embodiments, such as those wherein the hygienic device is intended for cats, the filler material may contain catnip and/or other cat attracting herbs.

In some embodiments, the filler material may include food to induce the animal to bite the device. In some such embodiments, the food filler material may exit the device (for example via the apertures or some other means) and be available to be eaten by the animal. In some embodiments, the filler material may be a material structured to engage the outer surface of the animal's tooth within the interior cavity and having a shape and sufficient hardness (and roughness) to scrape the outer surface and/or to provide additional frictional engagement to clean the tooth (e.g., brushes, bristles, wires, meshes, sponges etc. made of natural or synthetic materials, plastics, rubbers, elastomers, etc. and being of any suitable shape (e.g., circular, longitudinal, horizontal, spiral, etc.)).

In the context of the present technology filler materials are not limited to solids, as, for example, in some embodiments, the filler material may be or contain fluids such as liquids, gels, pastes, etc. or any suitable combination thereof. Thus, in some embodiments the interior cavity may serve as a reservoir for a fluid material to exit the device during chewing or biting and enter the mouth of the animal (without or along with solid particles also being part of the filler). Non-limiting examples of the functions of such fluids include toothpastes, mouth rinses, dental medicaments, other medicaments and medications, flavors, animal attractants, nutrients, vitamins etc. Almost any biocompatible fluid may be housed within the interior cavity (as long as it is not incompatible within any other component or filler of the device).

Filler is not limited to a single material; multiple non-incompatible materials are present as filler within the interior cavity in some embodiments. As a simple non-limiting example of a multiple material filler is a brush coated with a dental antibiotic.

In some embodiments, each aperture is at least one of structured, dimensioned, and positioned so as to discourage filler material from exiting the cavity via that aperture, be it generally or only cases where the animal is not chewing or biting the device. A non-limiting example of the latter is the case described hereinabove where the apertures are slits in which the side walls touch each other (effectively closing the apertures) until pressure from the animal's biting the hollow body causes a deformation which separates the side walls form one another, opening the apertures.

In some embodiments, the hollow body is sealed and replacement of the filler material is not possible. In some such embodiments, the entire device is biodegradable, recyclable and/or compostable.

In some embodiments, the hollow body has at least one releasably-attachable removable portion allowing access to the filler material in the cavity. In some such embodiments, once the removable portion attachment has been released and the removable portion has been removed, the filler material can be removed (if necessary) and new filler material (be it the same as or different from the old filler material) can be inserted into the interior cavity of the device. The removable portion can then be reattached and the device reused with the new filler material.

In some such embodiments, in order to facilitate removal and replacement of the filler material, the filler material is attached to the removable portion of the hollow body. Thus, when the removable portion is removed from the hollow body, the filler material is removed as well. Further, in some such embodiments, reinsertion of new filler material and the removable portion (be it the old removable portion to which the new filler material has been attached or a new removable portion having new filler material attached), is accomplished as a single unit.

In some embodiments, the device is dog-bone shaped. In some such embodiments, the at least one releasably-attachable removable portion is a flared-end of the dog-bone.

In some embodiments, the device is one of a rod, spherical, disc, and annular (e.g., doughnut) shape.

In some embodiments, is structured to be attachable to an animal toy.

In some embodiments, the device is at least part of an animal toy.

While most embodiments of the device of the present technology are intended for use by domestic animals, embodiments of the device may be constructed for use by other animals such as humans, feral animals or wild animals.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where:

FIG. 17*bis* is a close-up schematic cross-section of an aperture of the exterior surface of the hollow body through which a tooth of the animal has penetrated, shown schematically;

FIG. 18*bis* is a close-up schematic cross-section of an aperture of the exterior surface of the hollow body through which a tooth of the animal has penetrated, shown schematically;

DETAILED DESCRIPTION

Referring to the Figures, there are shown various animal dental hygienic devices of the present technology. It is to be expressly understood that the various animal dental hygienic devices are merely some embodiments of the present technology. Thus, the description thereof that follows is intended to be only a description of illustrative examples of the present technology. This description is not intended to define the scope or set forth the bounds of the present technology. In some cases, what are believed to be helpful examples of modifications to the animal dental hygienic devices may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of embodying that element of the present technology. As a person skilled in the art would understand, this is likely not the case. In addition, it is to be understood that the animal dental hygienic devices may provide in certain instances simple embodiments of the present technology, and that where such is the case they have been presented in this manner as an aid to understanding. As persons skilled in the art would understand, various embodiments of the present technology may be of a greater complexity.

Figure 1:
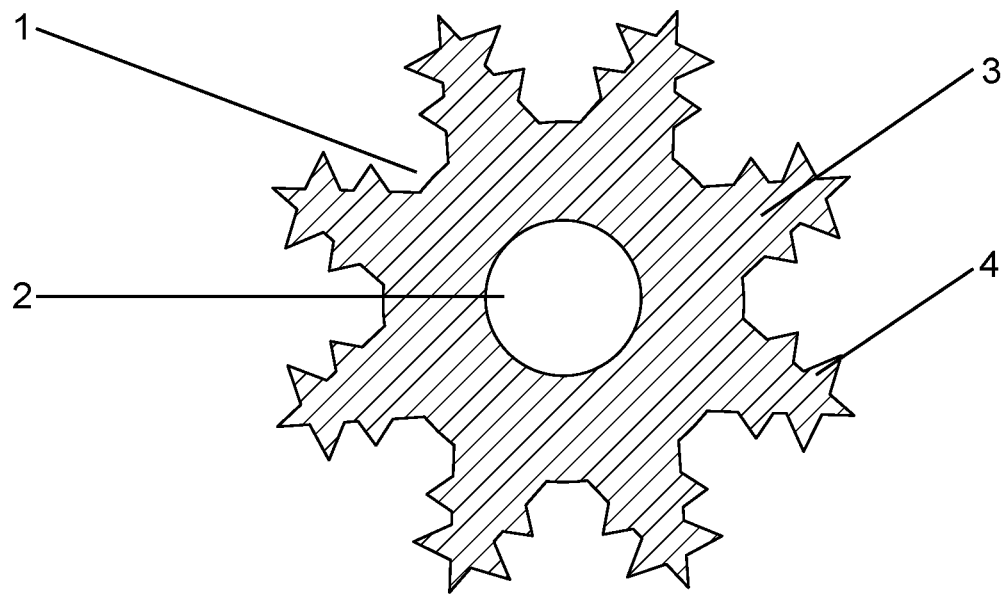
FIG. 1 is a transverse cross-section of an animal dental hygienic device being a first embodiment of the present technology.

FIG. 1 shows a transverse cross-section of an animal dental hygienic device being a first embodiment of the present technology. The device has a flexible plastic hollow body 1, having a circular interior cavity 2. Primary projections 3 extend radially away from the exterior surface of the hollow body 1. In this embodiment, primary projections 3 are made of the same flexible plastic as the hollow body 1. Extending from the primary projections 3 are secondary projections 4. In this embodiment, secondary projections 4 are made of the same flexible plastic as the hollow body 1 and the primary projections 3. In other embodiments, the primary projections 3 may comprise bristles, plastic, silicone, rubber, wood, etc. In other embodiments, a primary projection 3 may be bent or angled in such a way to form a secondary projection 4. In this embodiment, the primary projections 3 are triangular in shape when viewed in a transverse cross-section, with the base of the triangle at the exterior surface of the hollow body 1. In this embodiment, the primary projections 3 are flexibly rigid. In other embodiments, the primary projections (when present) are various different shapes and sizes and rigidities and flexibilities. In other embodiments, the surfaces of the primary projections 3 are roughened and/or contain and/or have attached to them chemical substances. Such chemical substances in various other embodiments are, by way of example, abrasives, additives, nutrients, etc. The primary projections 3 clean teeth, gums, and tongue of the animal, and in this embodiment the primary projections 3 help to guide the animal's teeth to engage the secondary projections 4 which are more numerous and have larger cleaning surface, thereby producing a more effective and efficient cleaning action than the primary projections 3 may otherwise produce by themselves. Apertures are not illustrated in this view.

Figure 2:
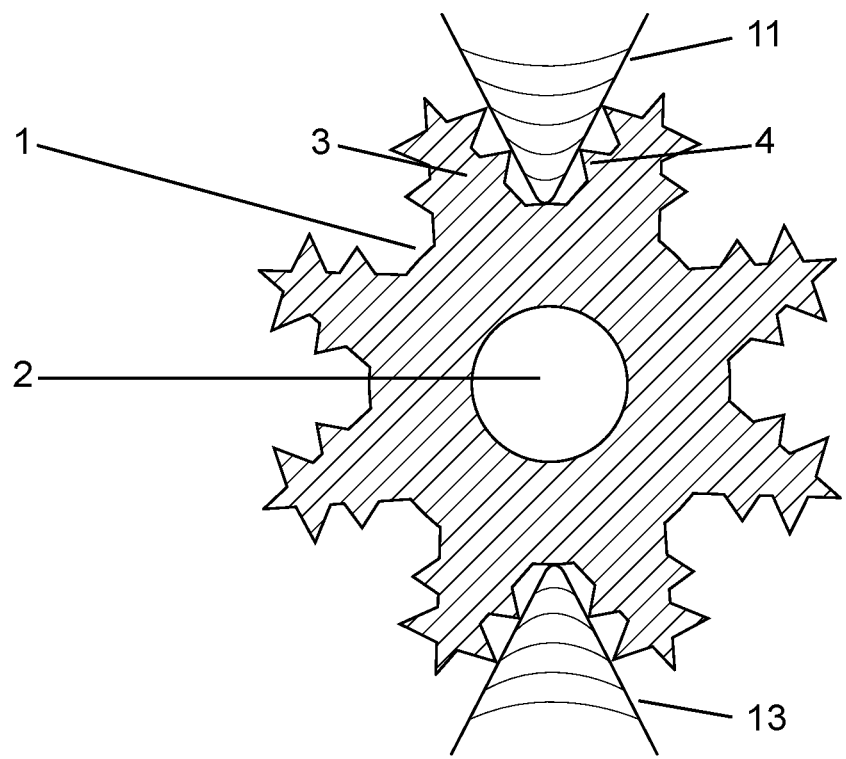
FIG. 2 is a transverse cross-section similar to FIG. 1, schematically showing animal teeth engaging the device.

FIG. 2 is a transverse cross-section similar to FIG. 1, schematically showing animal teeth (an upper tooth 11 and a lower tooth 13) engaging the device. Specifically, upper tooth 11 and lower tooth 13 are schematically shown at the moment of biting in the dental hygienic device. In this embodiment, the triangular shape of the primary projections 3 and the secondary projections 4 is selected to conform to most animal teeth (and indeed most human teeth), which are themselves triangular in shape.

Figure 3:
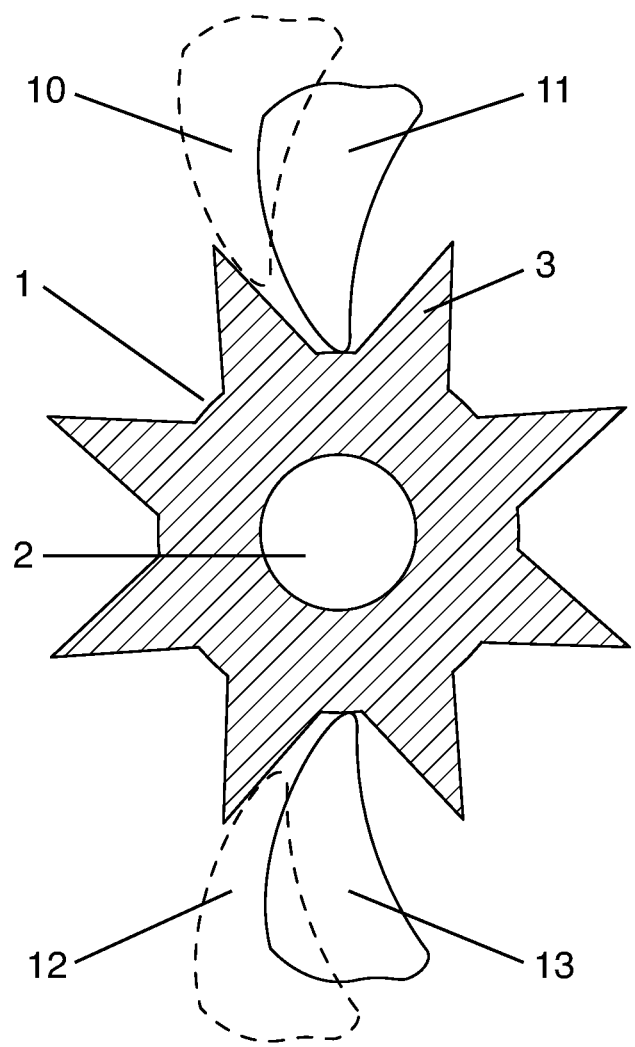
FIG. 3 is a transverse cross-section of an animal dental hygienic device being a second embodiment of the present technology, schematically showing animal teeth being guided along the surface of primary projections.

FIG. 3 is a transverse cross-section similar to FIG. 1, schematically showing animal teeth 10, 12 being guided along the surface of primary projections 3. Specifically, an upper tooth 10 and/or lower tooth 12 biting on a distal aspect of a primary projection 3, is guided towards the exterior surface of the hollow body 1, and in so doing allows for more effective cleaning by the secondary projections (where present), as well as preparing the biting force to engage (and penetrate) the hollow body 1. Upper tooth 11 and lower tooth 13 can be seen resting between primary projections 3 after having been guided by the slope of a primary projection 3.

Figure 4:
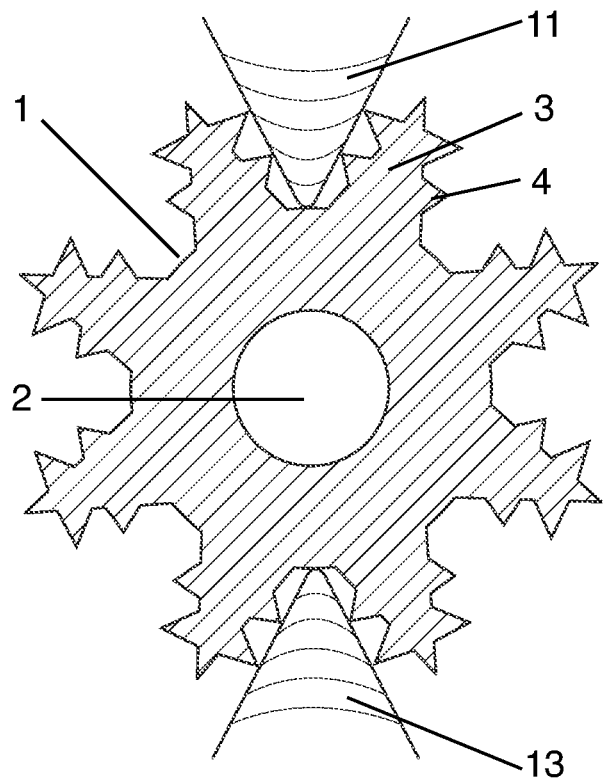
FIG. 4 is a transverse cross-section similar to FIG. 1, schematically showing animal teeth being cleaned by frictional engagement with secondary projections (projecting from primary projections projecting from the exterior surface of the hollow body thereof)

FIG. 4 illustrates the preferred biting position of teeth 11 and 13 between the primary projections 3 wedged between the secondary projections 4, engaging the hollow body 1 of the device.

Figure 5:
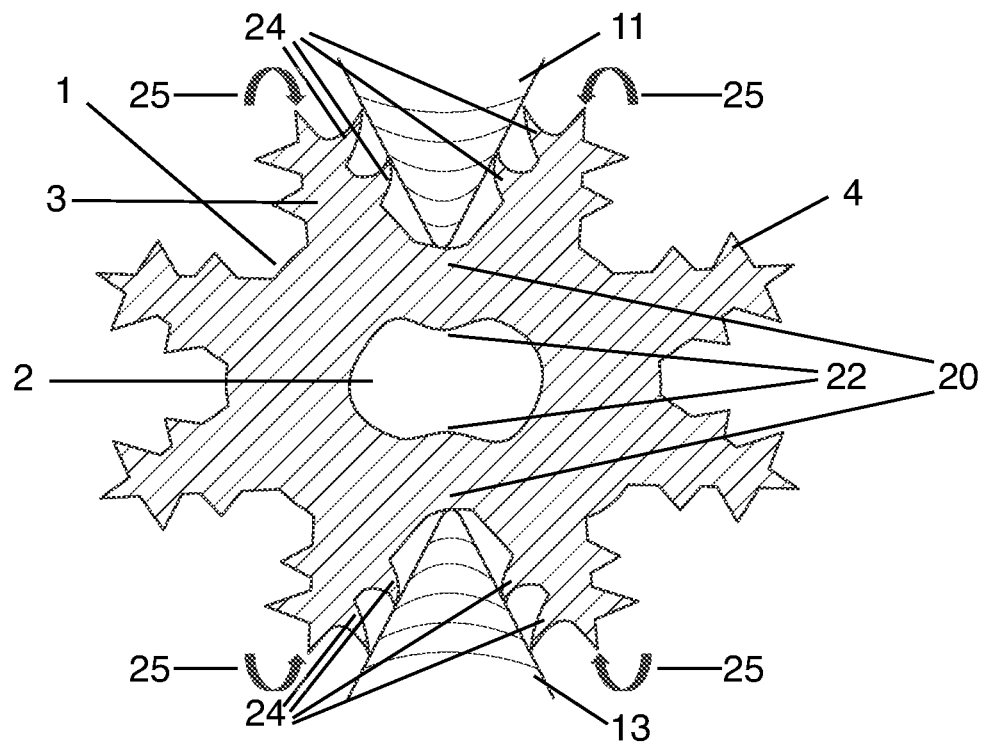
FIG. 5 is a transverse cross-section similar to FIG. 4, schematically showing animal teeth biting the flexible hollow body of the device causing deformation causing the primary projections to move towards the outer surfaces of the teeth causing the secondary projections to frictionally engage the outer surfaces of the teeth with greater force, enhancing the cleaning action of the secondary projections.

FIG. 5 demonstrates the biting force of upper 11 and lower 13 teeth engaging the flexible hollow body 1 (prior to penetration), causing a deformation 20 in the hollow body 1, and interior cavity 22. The deformation 20 causes the proximal displacement 25 of the primary projection 3 as well as the secondary projections 4 attached thereto, thereby creating an active cleaning movement on the part of both the primary projections 3 and secondary projections 4 (those of which that are moving are referenced as 24).

Figure 6:
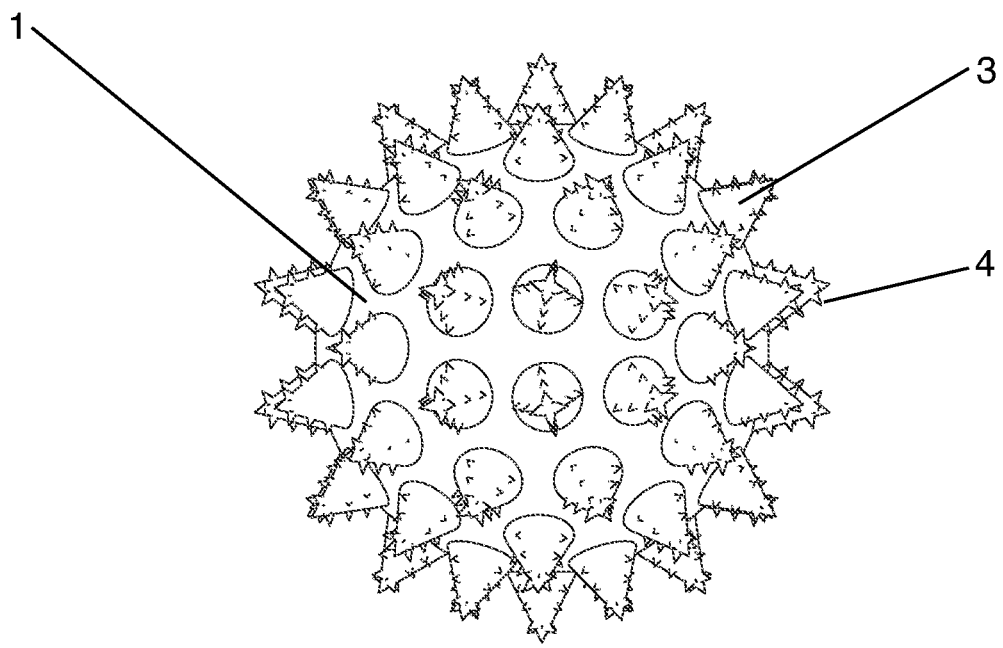
FIG. 6 is a side elevation view of an animal dental hygienic device in the form of a sphere (having primary and secondary projections projecting from the exterior surface of the hollow body thereof) being a third embodiment of the present technology.

FIG. 6 illustrates another embodiment of an animal dental hygienic device, which is spherical. In this embodiment, the same principal of guiding and cleaning by primary projections 3 being displaced proximally towards teeth 11 and 13 as a biting force is exerted is true. As was discussed above, this causes increased movement of and hence cleaning by the primary projections 3 and secondary projections 4 when the hollow body 1 of the device is round (as seen in FIG. 6) or rod-shaped (in whole or in part) as illustrated in FIGS. 7, 8, 9 and 10. Apertures are not illustrated in this view.

Figure 7:
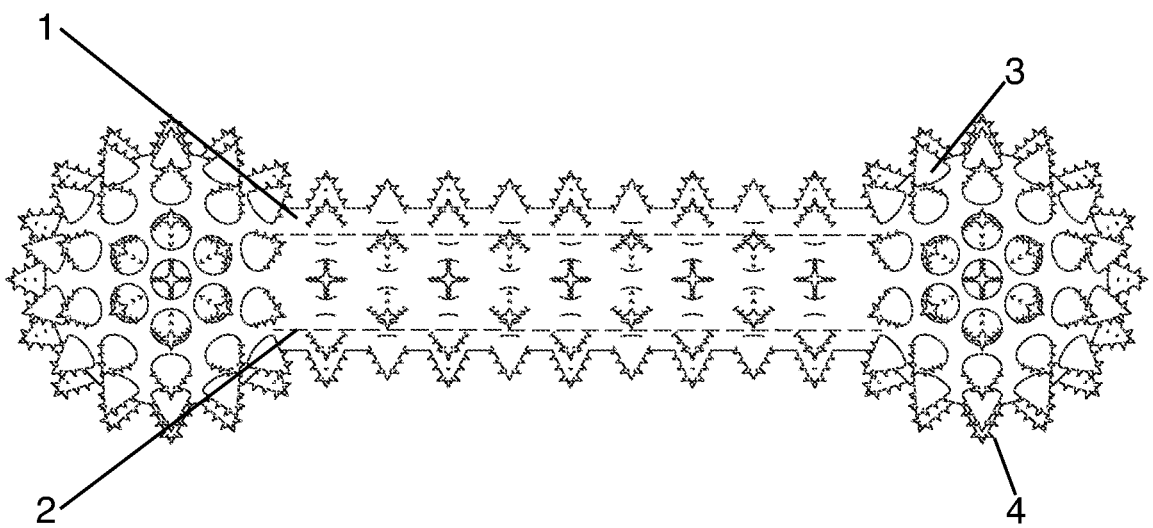
FIG. 7 is a side elevation view of an animal dental hygienic device in the form of "barbell" (a central right cylindrical rod having an interior cavity schematically shown in dotted lines and having spheres at each end) (having primary and secondary projections projecting from the exterior surface of the hollow body thereof) being a fourth embodiment of the present technology.
Figure 23:
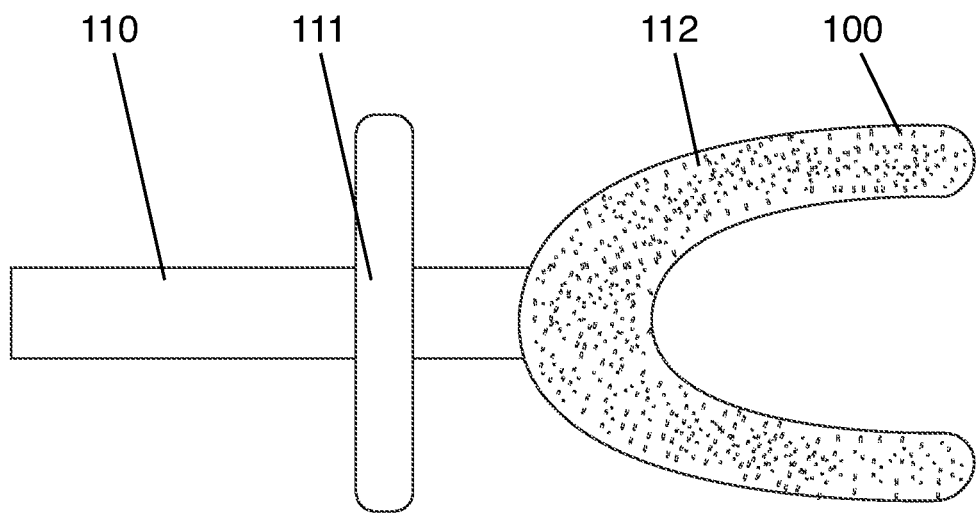
FIG. 23 shows a schematic top view of an animal dental hygienic device being a fifteenth embodiment of the present technology, being horseshoe-shaped and having a handle, showing toothbrush bristle like projections projecting from the exterior surface of the hollow body of the device.

FIG. 7 is a side elevation view with partial cross-section of an animal dental hygienic device in the form of "barbell" (a central right cylindrical rod having spheres at each end) (having primary projections 3 and secondary projections 4 projecting from the exterior surface of the hollow body 1 thereof) being another embodiment of the present technology. The interior cavity 2 of the hollow body 1, shown in dotted lines, serves as a reservoir which may contain any one or more of various solids, liquids or gels. A handle may be attached to one end of the device so that the device can be moved over the teeth of the animal in a brushing motion by a human (e.g., as illustrated in FIG. 23). Apertures are not illustrated in this view.

Figure 8:
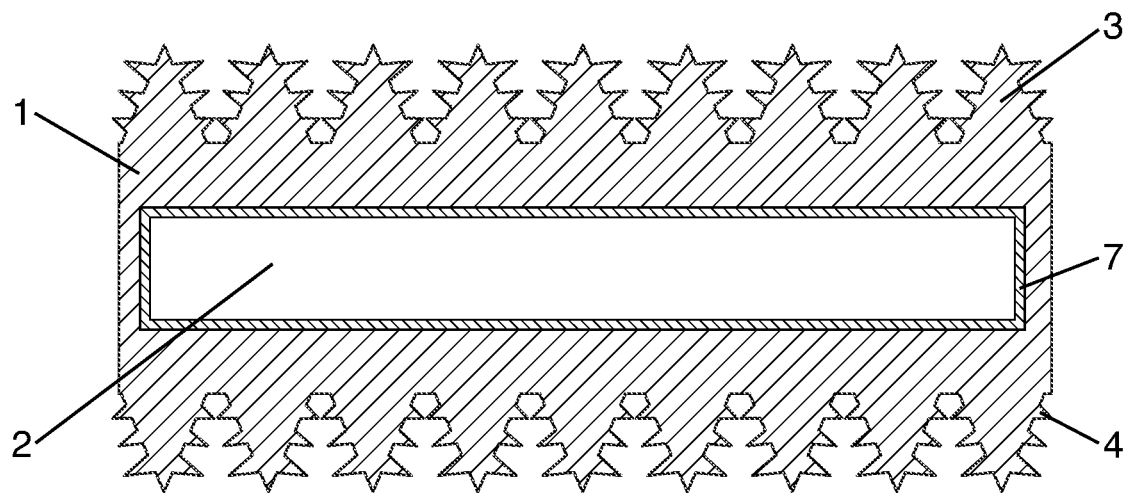
FIG. 8 is a longitudinal cross-section of an animal dental hygienic device in the form of a right cylindrical rod (having primary and secondary projections projecting from the exterior surface of the hollow body thereof) showing the interior cavity of the hollow body thereof lined with a membrane and forming a reservoir, being a fifth embodiment of the present technology.

FIG. 8 is a longitudinal cross-section of an animal dental hygienic device in the form of a right cylindrical rod (having primary projections 3 and secondary projections 4 projecting from the exterior surface of the hollow body 1 thereof) showing the interior cavity 2 of the hollow body 1 thereof. In this embodiment, the interior cavity 2 is lined with a membrane 7 sealing the interior cavity 2 to form a reservoir. Apertures are not illustrated in this view.

Figure 9:
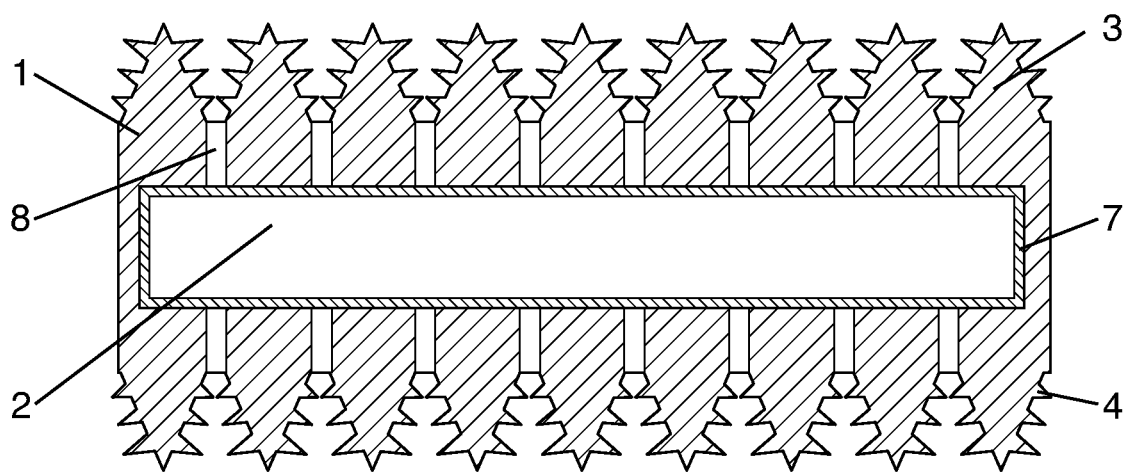
FIG. 9 is a longitudinal cross-section similar to FIG. 8 showing apertures (channels) through the hollow body to the exterior surface thereof, being a sixth embodiment of the present technology.

FIG. 9 is a longitudinal cross-section similar to FIG. 8 showing apertures (in this embodiment in the form of cylindrical "tube-like" channels) 8 from the membrane 7 lining the interior cavity 2 and through the hollow body 1 to the exterior surface thereof. The apertures 8 are located on the exterior surface of the hollow body 1 between the primary projections 3. As teeth bite the device, prior to penetration, pressure is exerted against the hollow body 1 of the device, thereby expressing material contained in the interior cavity 2 therein through the membrane 7 and through the apertures 8. In this embodiment, the apertures 8 are open on both ends (through the hollow body 1) and an appropriately sized material (e.g., a fragrance, a medicament, a nutrient, etc., or any combination thereof) is placed into the interior cavity 2. Thus, saliva from the animal will enter the interior cavity 2 either prior to or after penetration of the apertures 8 by the teeth of the animal and will interact with the material which will be released into the mouth of the animal.

Figure 10:
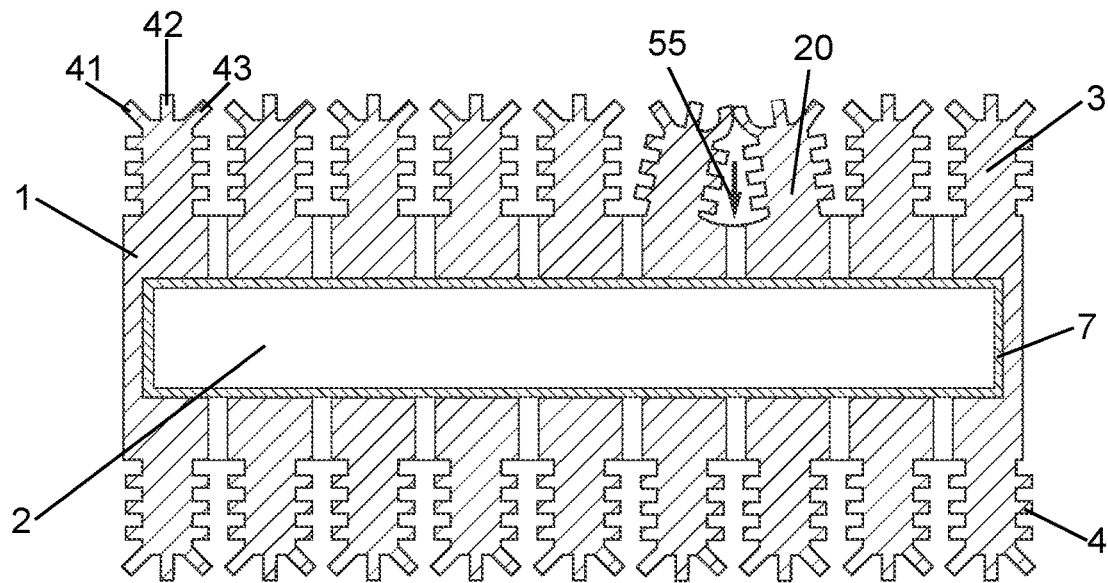
FIG. 10 is a longitudinal cross-section similar to FIG. 9 showing a device being a seventh embodiment of the present technology having cylindrical primary and secondary projections.

FIG. 10 is a longitudinal cross-section similar to FIG. 9 showing a device being another embodiment of the present technology. In this embodiment, the primary projections 3 and the secondary projections 4 are cylindrical. Also in this embodiment, secondary projections 41, 42, 43 extend from the distal end of the primary projections 3. Optionally, the secondary projections 4 (and/or 41, 42, 43) may include brush bristles. Also in this embodiment, the secondary projections may be constructed of one or more of the following: plastic, silicone, nylon, rubber, a mineral (e.g. calcium) or a nutrient. The motion and force of an upper tooth biting the device is schematically represented in FIG. 10 by an arrow 55. The force generated causes the deformation 20 of primary projections 3, inward towards the tooth (not shown, which may engage the device at a point that is either before or past the cross-section plane of FIG. 10) in order to enhance the cleaning action of the primary projections 3 and the second projections 4.

Figure 11:
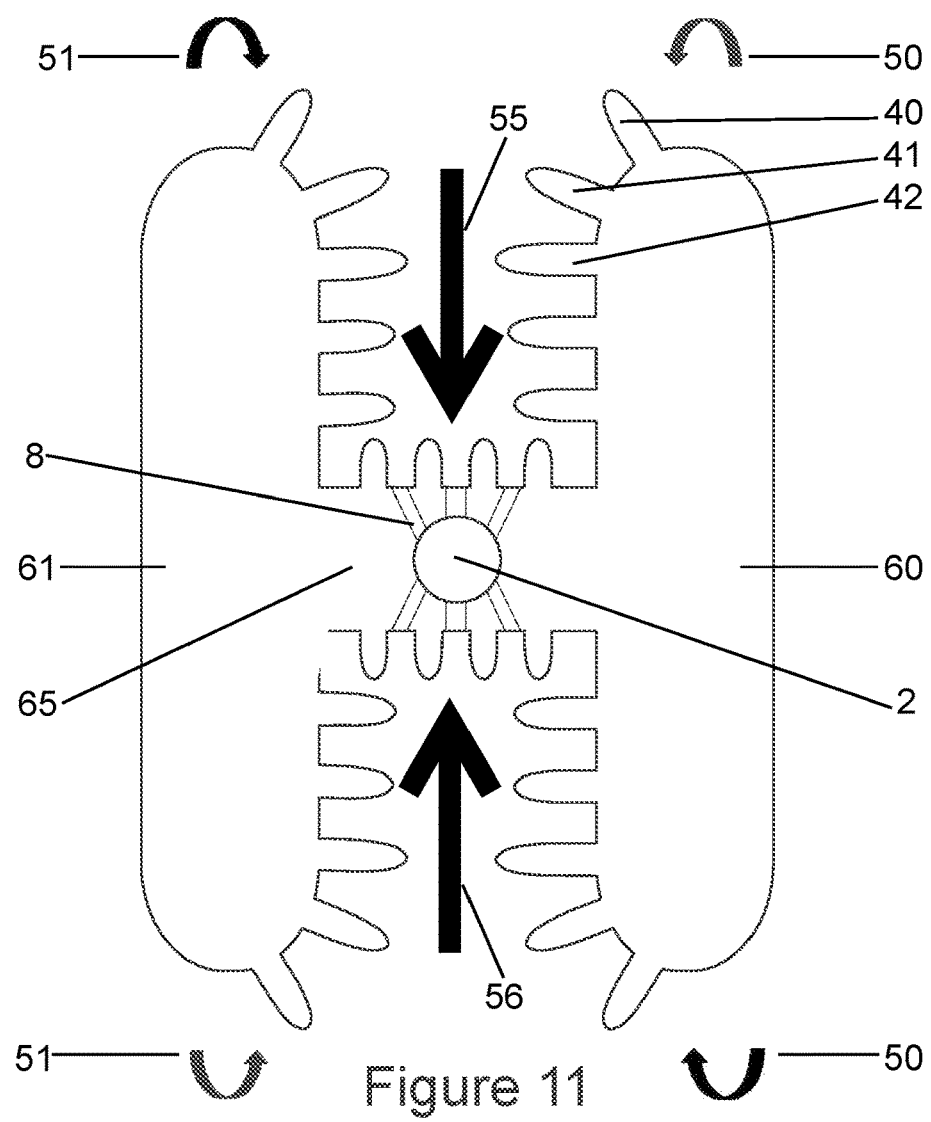
FIG. 11 is a cross-section showing a dental hygienic device being an eighth embodiment of the present technology being particularly adapted for use by a human, having vertical and horizontal cylindrical projections.
Figure 12:
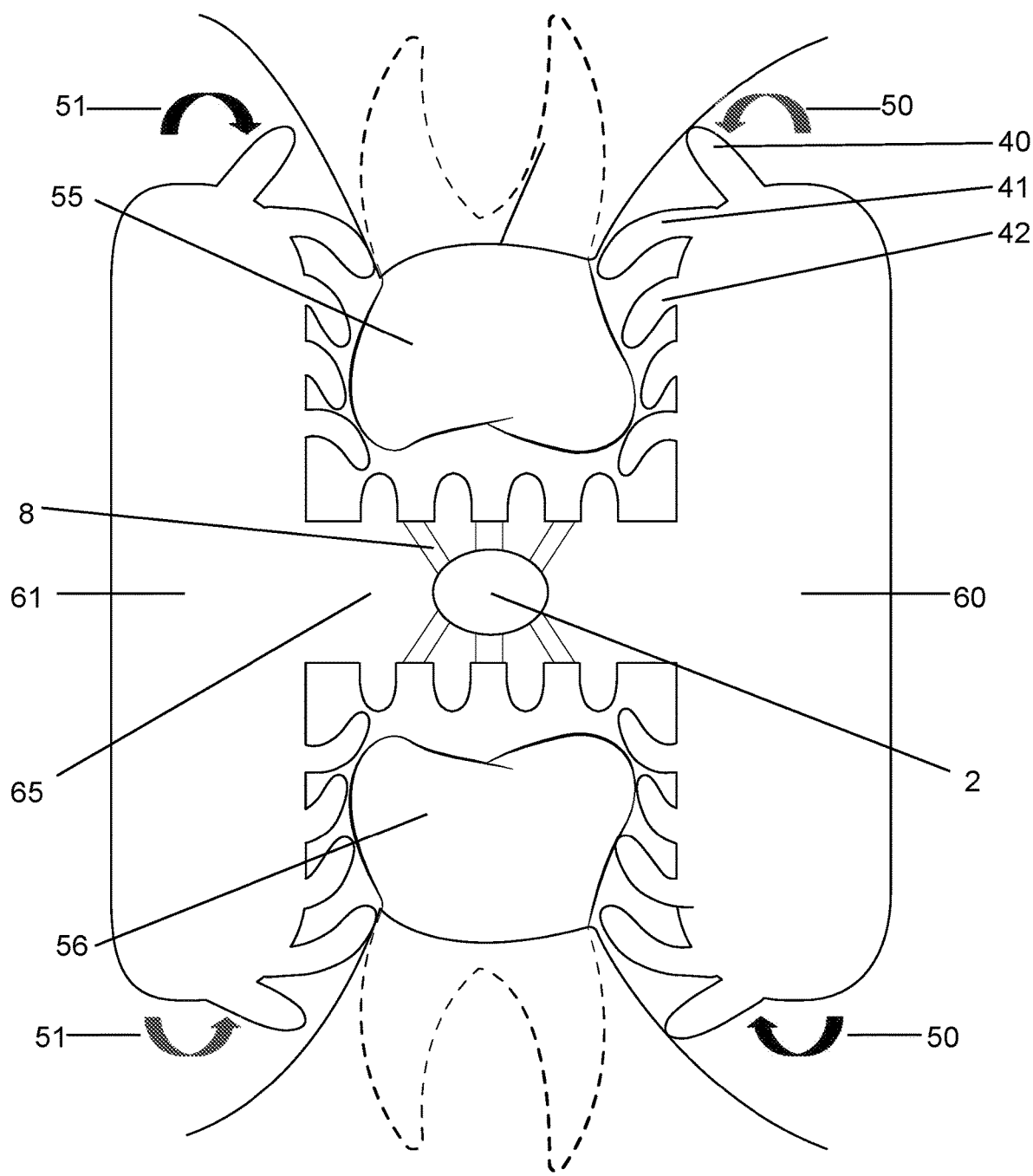
FIG. 12 is a cross-section similar to FIG. 11 schematically showing human teeth entering the device.

FIGS. 11 and 12 are cross-sections showing a dental hygienic device being another embodiment of the present technology being particularly adapted for use by a human. The hollow body 1 of the device in this embodiment has a transverse cross-section in the form of an "H" that is dimensioned to fit between upper teeth (55 shown in FIG. 12 and schematically in FIG. 11) and lower teeth (56 shown in FIG. 12 and schematically in FIG. 11). The hollow body 1 has a facial (distal) side flange 60 and an oral side flange 61. In this embodiment, the interior cavity 2 serves as a reservoir a material that will exit from the interior cavity 2 and deposited onto the teeth 55 and 56 via apertures (prior to penetration) 8. A force exerted will be exerted on the central connecting portion 65 of the "H"-shaped hollow body 1 by the upper teeth 55 and the lower teeth 56 coming together during chewing or biting causes an inward movement 50 and 51 of part 30 of the flange portions of the "H" 60, 61 thereby causing a cleaning movement of the secondary projections 40, 41, 42 against the teeth and other oral structures. Furthermore, as this force is exerted onto the reservoir formed by the interior cavity 2 of the hollow body 1, material inside the interior cavity will exit via the apertures 8 as was described hereinabove in relation to other embodiments. As teeth 55, 56 penetrate the apertures 8, they will be cleaned by being scraped by the material surround the apertures 8. Also in this embodiment, the secondary projections 4 may be constructed of one or more of the following: plastic, silicone, nylon, wood, rubber, a mineral (e.g. calcium) or a nutrient. Secondary projections 4 may optionally be edible.

Figure 13:
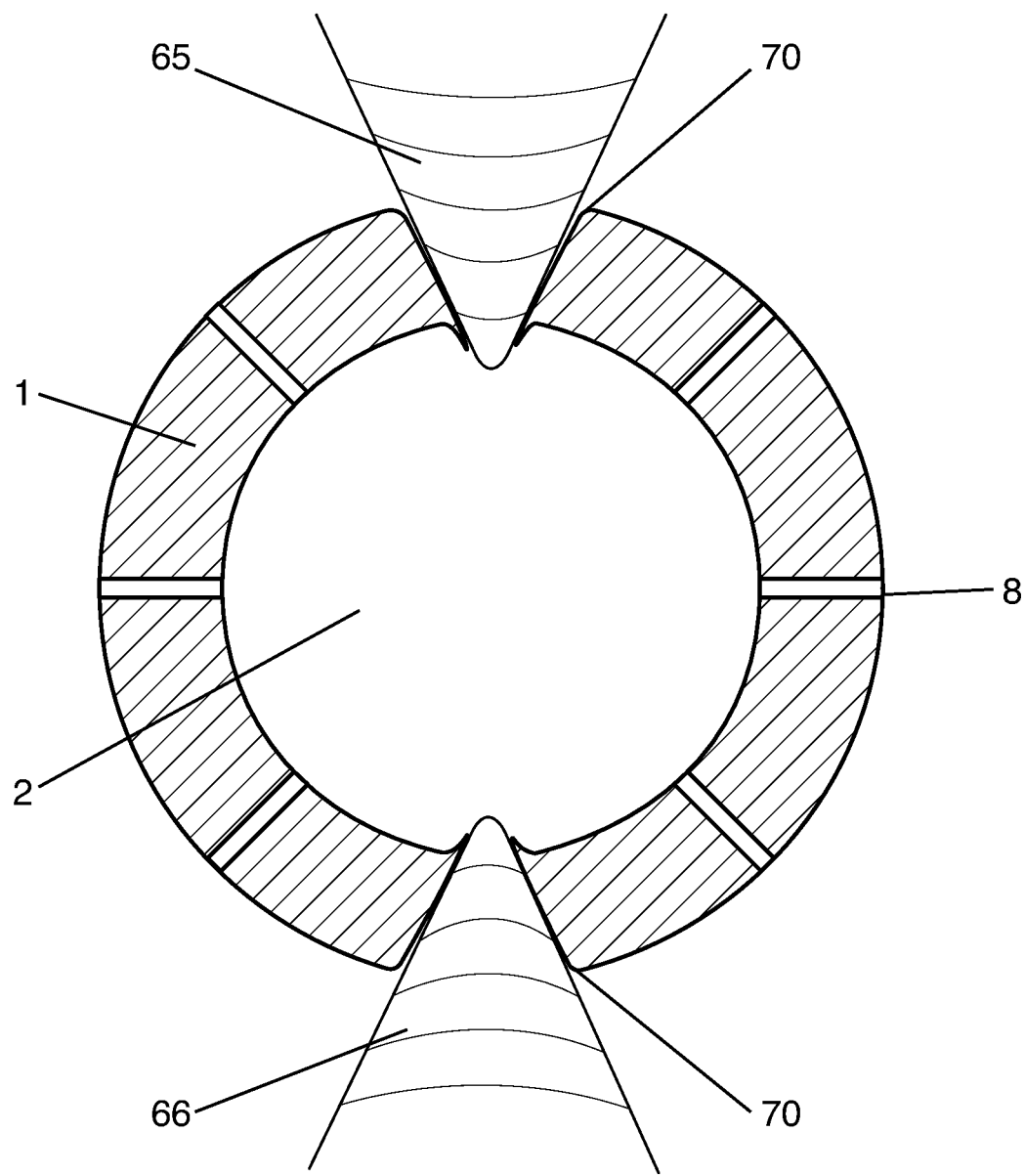
FIG. 13 is a schematic cross section of an animal dental hygienic device being a ninth embodiment of the present technology, schematically showing teeth of the animal penetrating apertures of the device.

FIG. 13 is a schematic cross section of an animal dental hygienic device being another embodiment of the present technology, schematically showing an upper tooth 65 and a lower tooth 66 of the animal having penetrated and deformed apertures 70 of the device.

Figure 14:
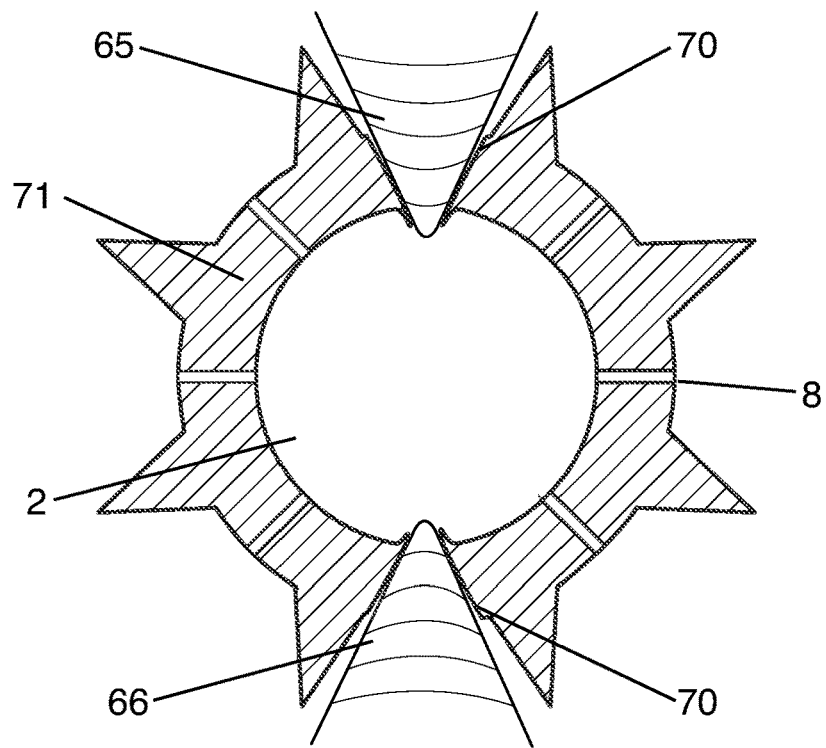
FIG. 14 is schematic cross-section of an animal dental hygienic device being an tenth embodiment of the present technology, including projections, schematically showing teeth of the animal penetrating apertures of the device.

FIG. 14 is schematic cross-section of an animal dental hygienic device being another embodiment of the present technology, including primary projections 3 as were described hereinabove in relation to other embodiments. An upper tooth 65 and a lower tooth 66 of the animal are schematically shown penetrating and deforming apertures 70 of the device. The device has a hollow body 71 and an interior cavity 2.

Figure 15:
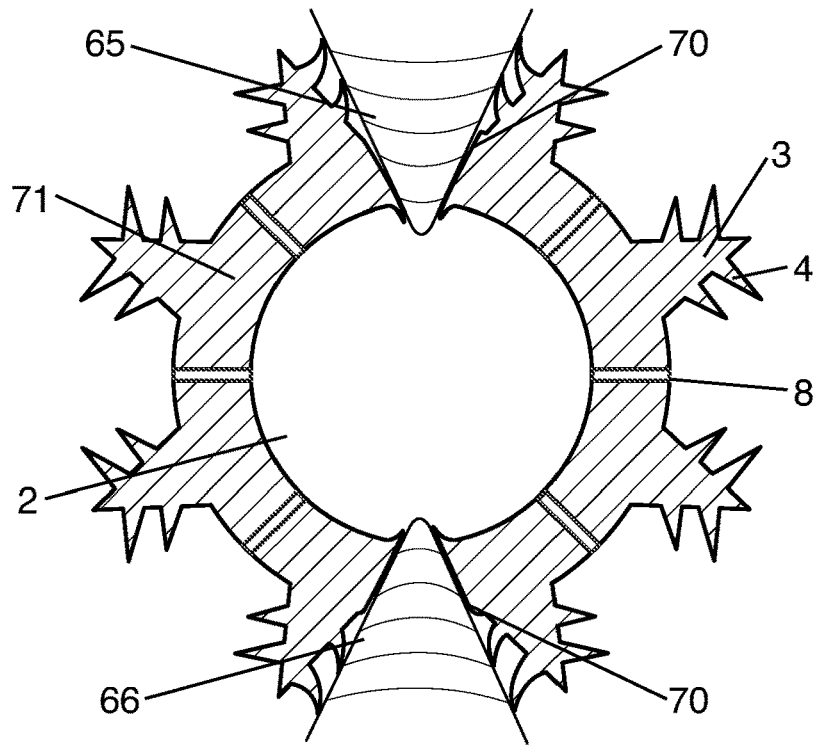
FIG. 15 is schematic cross-section of an animal dental hygienic device being an eleventh embodiment of the present technology, including primary and secondary projections, schematically showing teeth of the animal penetrating apertures of the device.

FIG. 15 is schematic cross-section of an animal dental hygienic device being another embodiment of the present technology, including primary projections 3 and secondary projections 4 as were described hereinabove in relation to other embodiments. An upper tooth 65 and a lower tooth 66 of the animal are schematically shown penetrating deformed apertures 70 of the device. The device has a hollow body 71 and an interior cavity 2.

Figure 16:
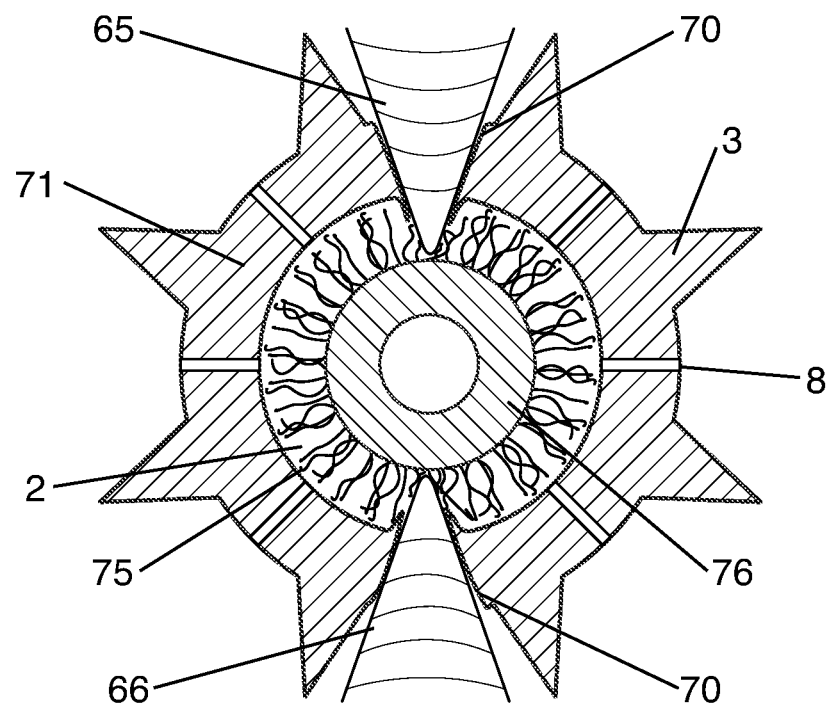
FIG. 16 is a transverse cross-section of an animal dental hygienic device being a twelfth embodiment of the present technology, including primary projections, schematically showing teeth of the animal penetrating apertures of the device; there being a circular brush with bristles in the interior cavity of the hollow body of the device to assist in cleaning the teeth.

FIG. 16 is schematic cross-section of an animal dental hygienic device being another embodiment of the present technology, including primary projections 3 as were described hereinabove in relation to other embodiments. The device has a hollow body 71 and an interior cavity 2. Inside the interior cavity 2, is a brush 76 having bristles 75. An upper tooth 65 and a lower tooth 66 of the animal are schematically shown penetrating deformed apertures 70 of the device. Once a tooth 65 and/or 66 is within the interior cavity 2 it will contact the bristles 75 of the brush 76 which will assist in cleaning the tooth. Optionally, the bristles 75 of the brush 76 may extrude through the apertures 8 and deformed apertures 70 as the device is chewed in order to additionally clean teeth and gums of the animal.

Figure 17:
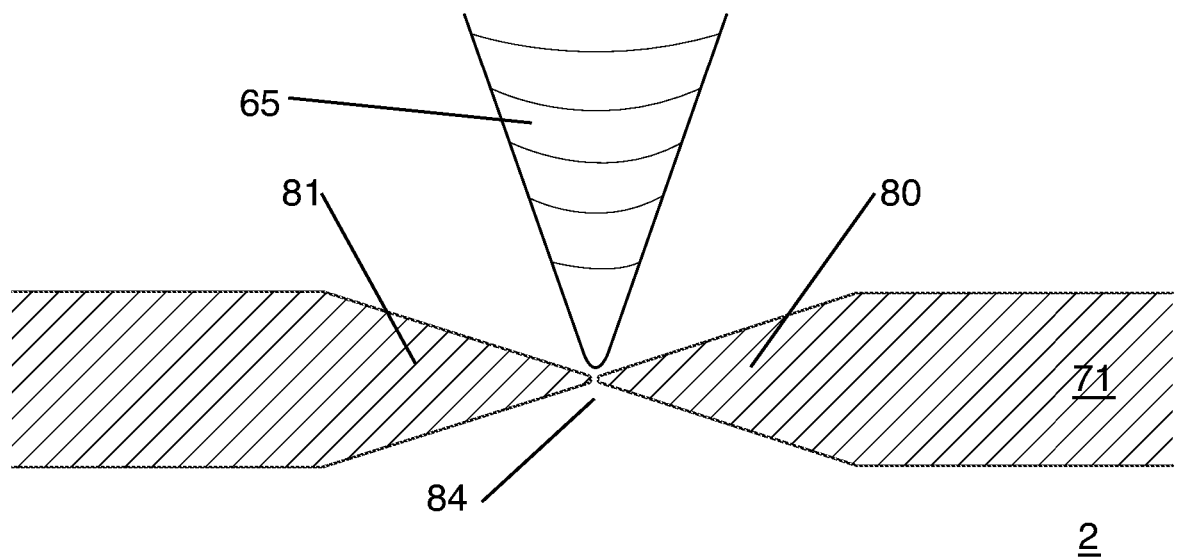
FIG. 17 is a close-up schematic cross-section of an aperture of the exterior surface of the hollow body through which a tooth of the animal may penetrate, along with an upper tooth of the animal.

FIG. 17 is a close-up schematic cross-section of an aperture 84 of the exterior surface of the hollow body through which an upper tooth 65 of the animal may penetrate, along with an upper tooth 65 of the animal. In this embodiment, the material at the edge 80, 81 of the aperture 84 has a cross-section that is triangular in shape. In other embodiments, the material at the edge 80, 81 of the aperture 84 has a cross-section that is rectangular or another geometric form in shape. FIG. 17*bis* schematically shows the upper tooth 65 penetrating the deformed aperture 84.

Figure 18:
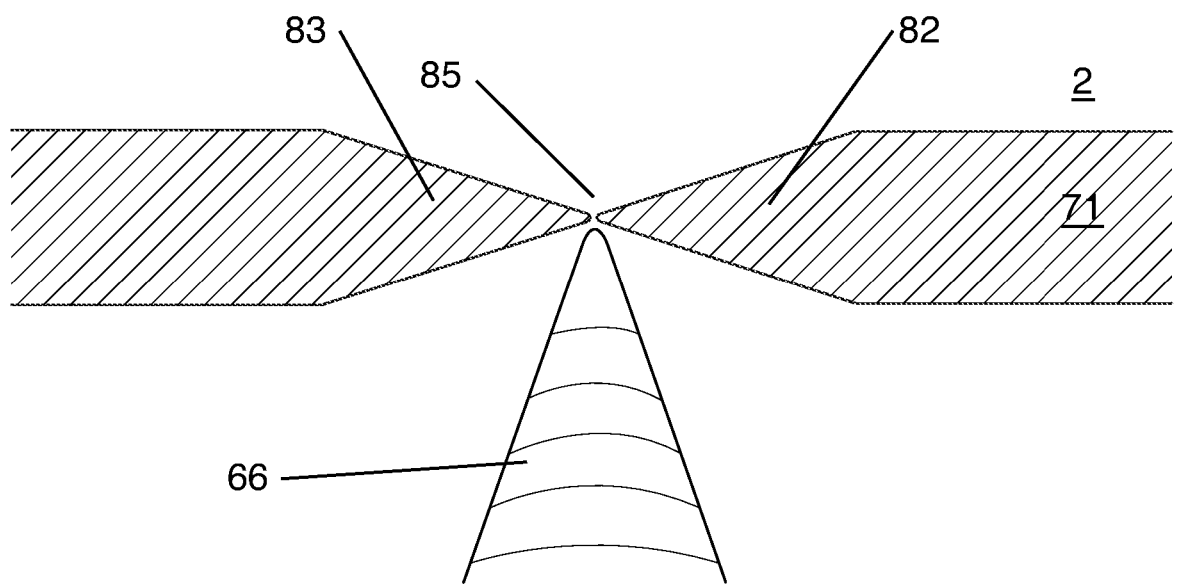
FIG. 18 is a close-up schematic cross-section of an aperture of the exterior surface of the hollow body through which a tooth of the animal may penetrate, along with a lower tooth of the animal.

FIG. 18 is a close-up schematic cross-section of an aperture 85 of the exterior surface of the hollow body through which a lower tooth 66 of the animal may penetrate, along with a lower tooth 66 of the animal. In this embodiment, the material at the edge 82, 83 of the aperture 85 is triangular in shape. In other embodiments, the material at the edge 82, 83 of the aperture 85 is rectangular or another geometric form in shape. FIG. 18*bis* schematically shows the lower tooth 66 penetrating the deformed aperture 70.

Figure 19:
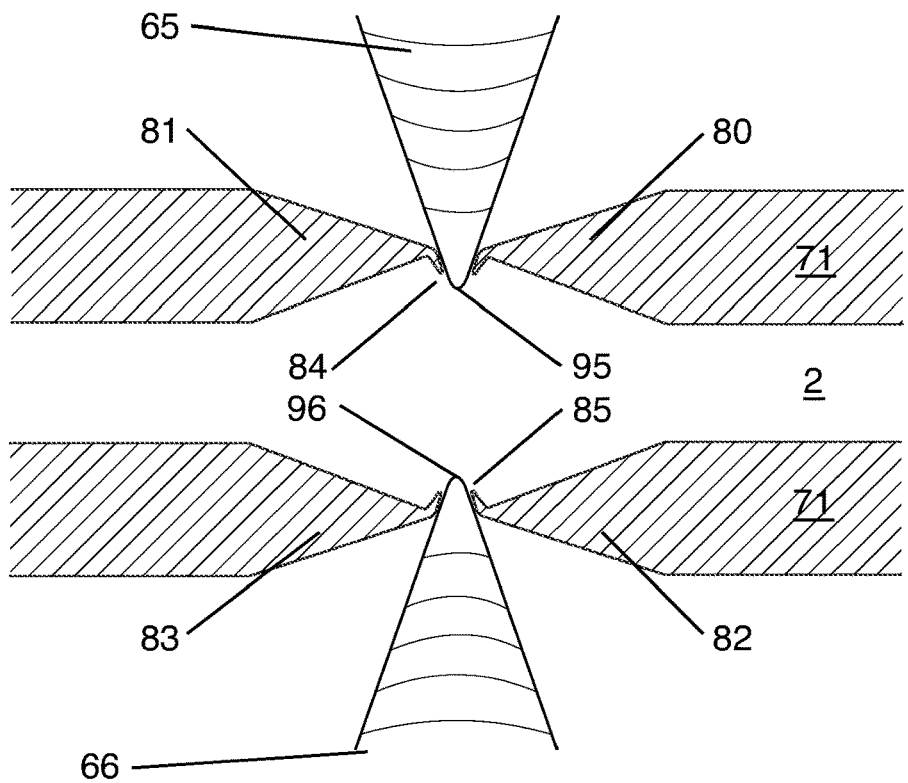
FIG. 19 is a close-up schematic cross-section similar to both FIGS. 17 and 18, schematically showing upper and lower teeth of the animal penetrating the apertures.

FIG. 19 is a combination of FIGS. 17*bis* and 18*bis*, schematically showing the incisal edge 95 of the upper tooth 65 and the incisal edge 96 of the lower tooth 66 being within the interior cavity 2 of the hollow body 71 of the device.

Figure 20:
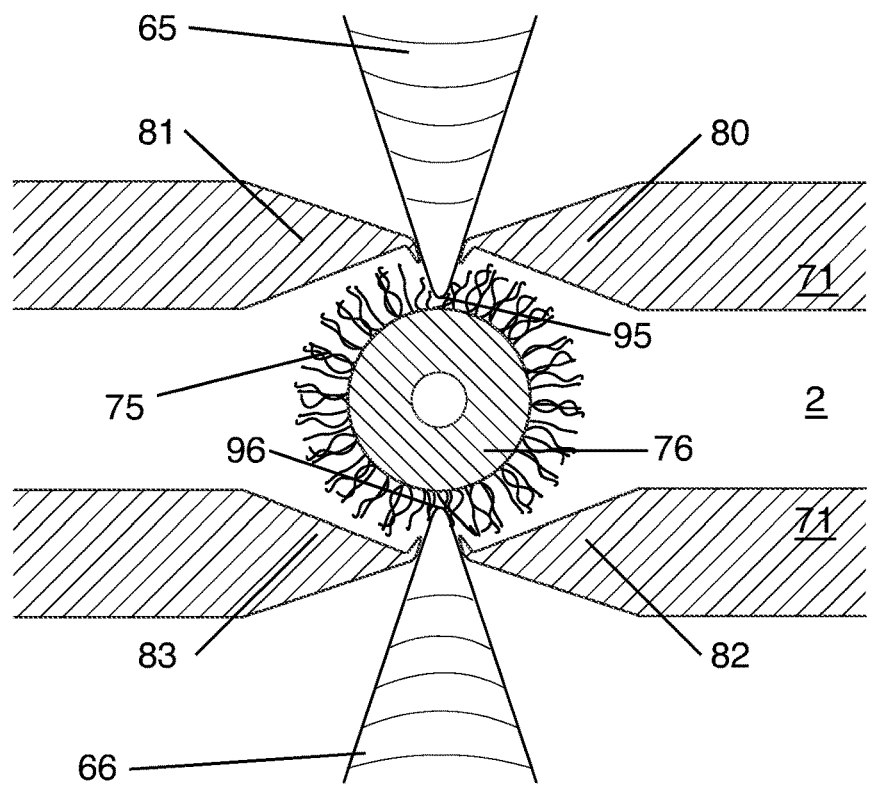
FIG. 20 is a close-up schematic cross-section similar to FIG. 19 schematically showing the portions of the teeth of the animal having penetrated within the interior cavity of the hollow body being cleaned by a brush within the interior cavity.

FIG. 20 is similar to FIG. 19, schematically showing the incisal edges 95, 96 contacting the bristles 75 of a brush 76 within the interior cavity 2 of the hollow body 71 of the device, for additional cleaning.

Figure 21:
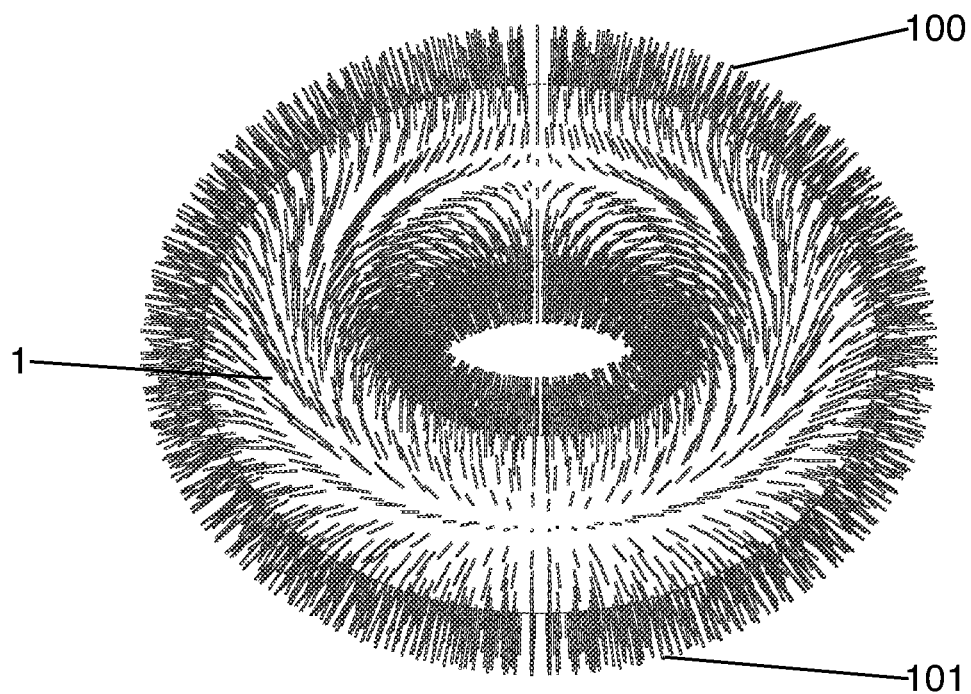
FIG. 21 shows a schematic view of an animal dental hygienic device being an thirteenth embodiment of the present technology, being ring-shaped, showing toothbrush bristle like projections projecting from the exterior surface of the hollow body of the device.

FIG. 21 shows a schematic view of an animal dental hygienic device being another embodiment of the present technology, the device being ring-shaped. In this embodiment, toothbrush bristle like projections 100, 101 project from the exterior surface of the hollow body 1 of the device. Projections 100 clean the maxillary teeth (not shown) when the device is chewed and projections 101 clean the mandibular teeth (not shown) when the device is chewed.

Figure 22:
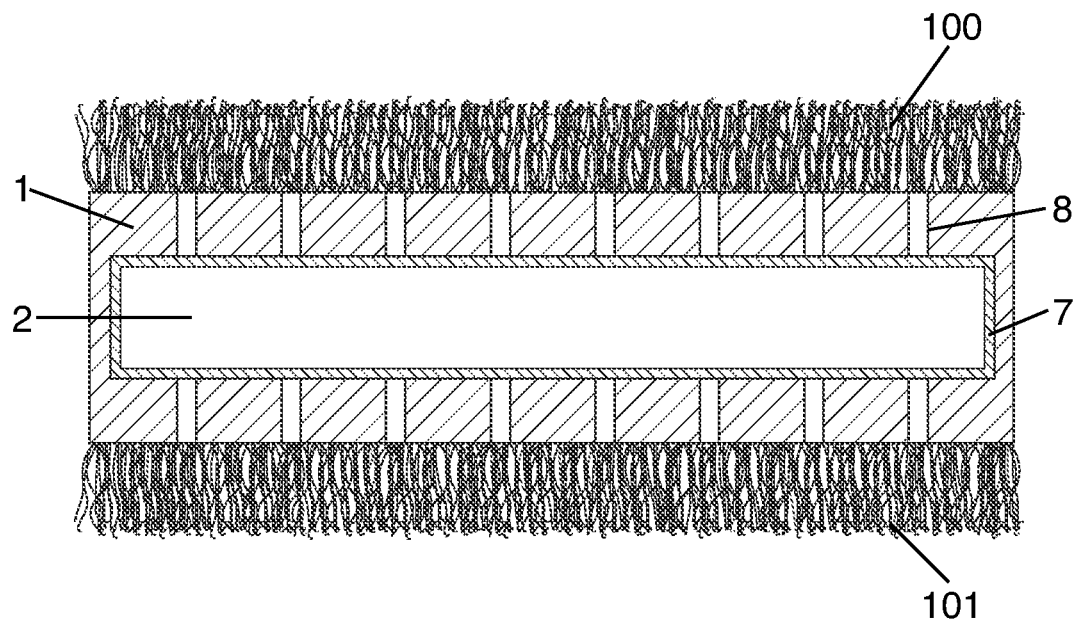
FIG. 22 shows a schematic longitudinal cross-section of an animal dental hygienic device being a fourteenth embodiment of the present technology, showing toothbrush bristle like projections projecting from the exterior surface of the hollow body of the device.

FIG. 22 shows a schematic longitudinal cross-section of an animal dental hygienic device being an embodiment of the present technology, with the interior structure of the device being similar to that shown in FIG. 8. In this embodiment, toothbrush bristle like projections 100, 101 project from the exterior surface of the hollow body 1 of the device. Projections 100 clean the maxillary teeth when the device is chewed and projections 101 clean the mandibular teeth when the device is chewed.

FIG. 23 shows a schematic view of an animal dental hygienic device being another embodiment of the present technology. In this embodiment, the hollow body 112 of the device is horseshoe-shaped and conforms to the jaws of an animal (e.g., a dog, a cat, livestock, etc.) for which the device is designed to be used. The device has handle 110 for placing the device into the mouth of an animal. A guard 111 helps to protect a person holding the handle from being accidentally bit. Toothbrush bristle like projections 100 project from the exterior surface of the hollow body of the device for additional cleaning.

Figure 24:
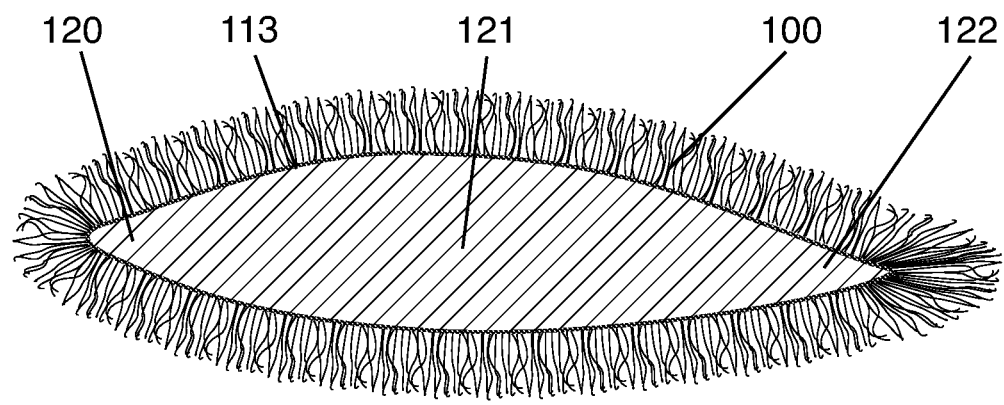
FIG. 24 shows a schematic longitudinal cross-section of an animal dental hygienic device being a sixteenth embodiment of the present technology, being shaped to fit the teeth contours of a cat's or dog's (the proximal and distal aspects are thinner than the middle of the device which coincides with the forms and occlusion of the animal's incisors, molars and bicuspids respectively), showing toothbrush bristle like projections projecting from the exterior surface of the hollow body of the device.

FIG. 24 shows a schematic longitudinal cross-section of an animal dental hygienic device being an embodiment of the present technology. In this embodiment, the device is shaped to fit the teeth contours of a cat's or dog's (the proximal and distal aspects 120, 122 (respectively) are thinner than the middle of the device 121 (which bulges) to coincide with the form and occlusion of the animal's incisors, molars and bicuspids respectively). Toothbrush bristle like projections 100 project from the exterior surface of the hollow body 113 of the device for additional cleaning.

With reference to FIGS. 25-44 and 51-54 there is shown an animal dental hygienic device 200 being another embodiment of the present technology. The device 200 has a hollow body 206 having an exterior surface 210 and an interior cavity 202 therein. The device 200 is made of a flexible (when bitten by a dog) thermoplastic elastomer, styrene butadiene block copolymer—modified with polypropylene. The device 200 has the shape of a "dog-bone" which is sized to fit into the mouth of a medium to large sized dog. The device 200 has two flared ends 214, 218 and a central section (unlabelled).

Figure 43:
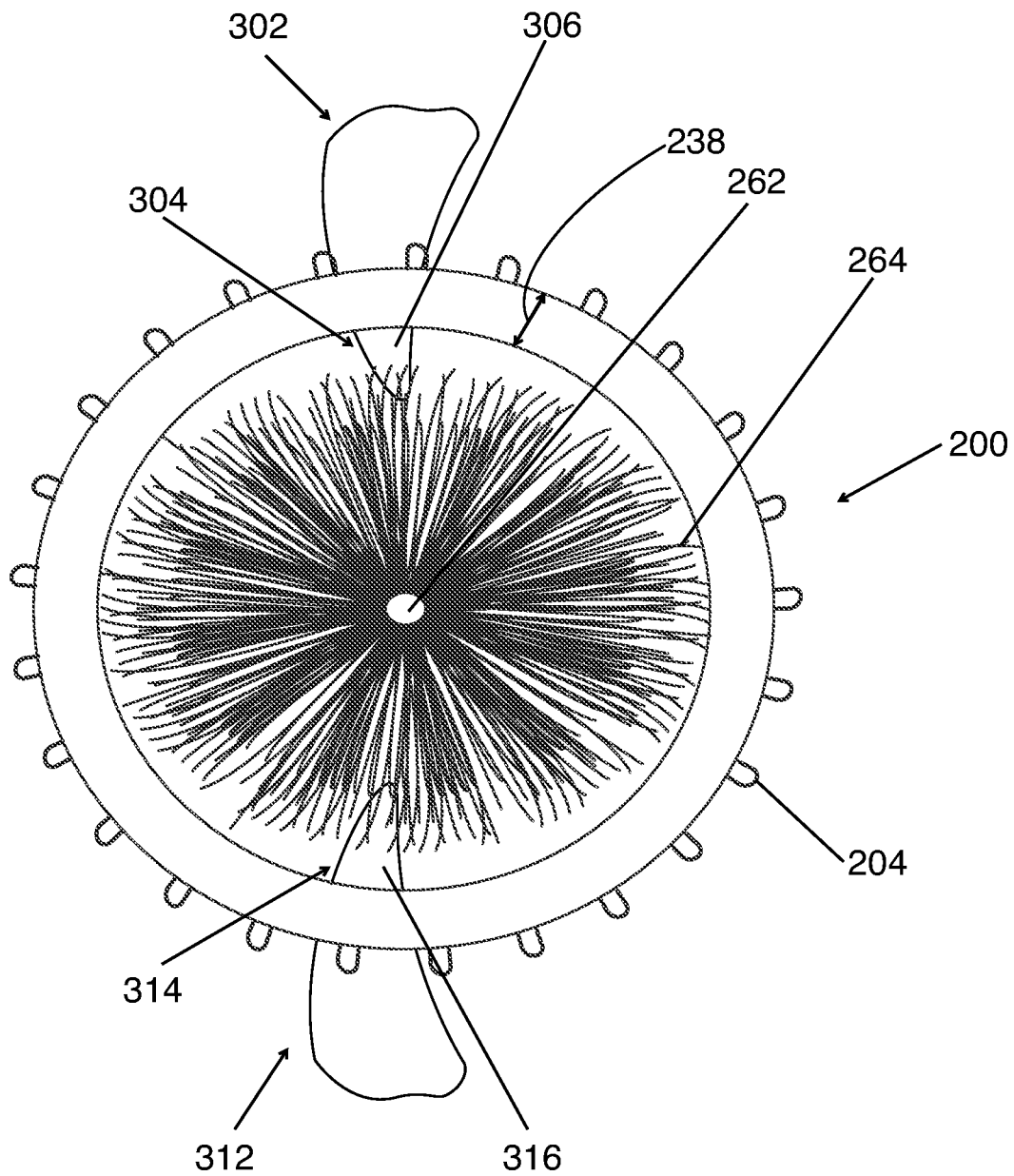
FIG. 43 is an elevation view of the attachment end of the remainder of the device of FIG. 25 as shown in FIG. 26, after a releasably-attachable removable portion of the hollow body has been detached from the remainder, showing a brush with bristles in the interior cavity thereof, and showing teeth of a dog penetrating the device and contacting the bristles.
Figure 52:
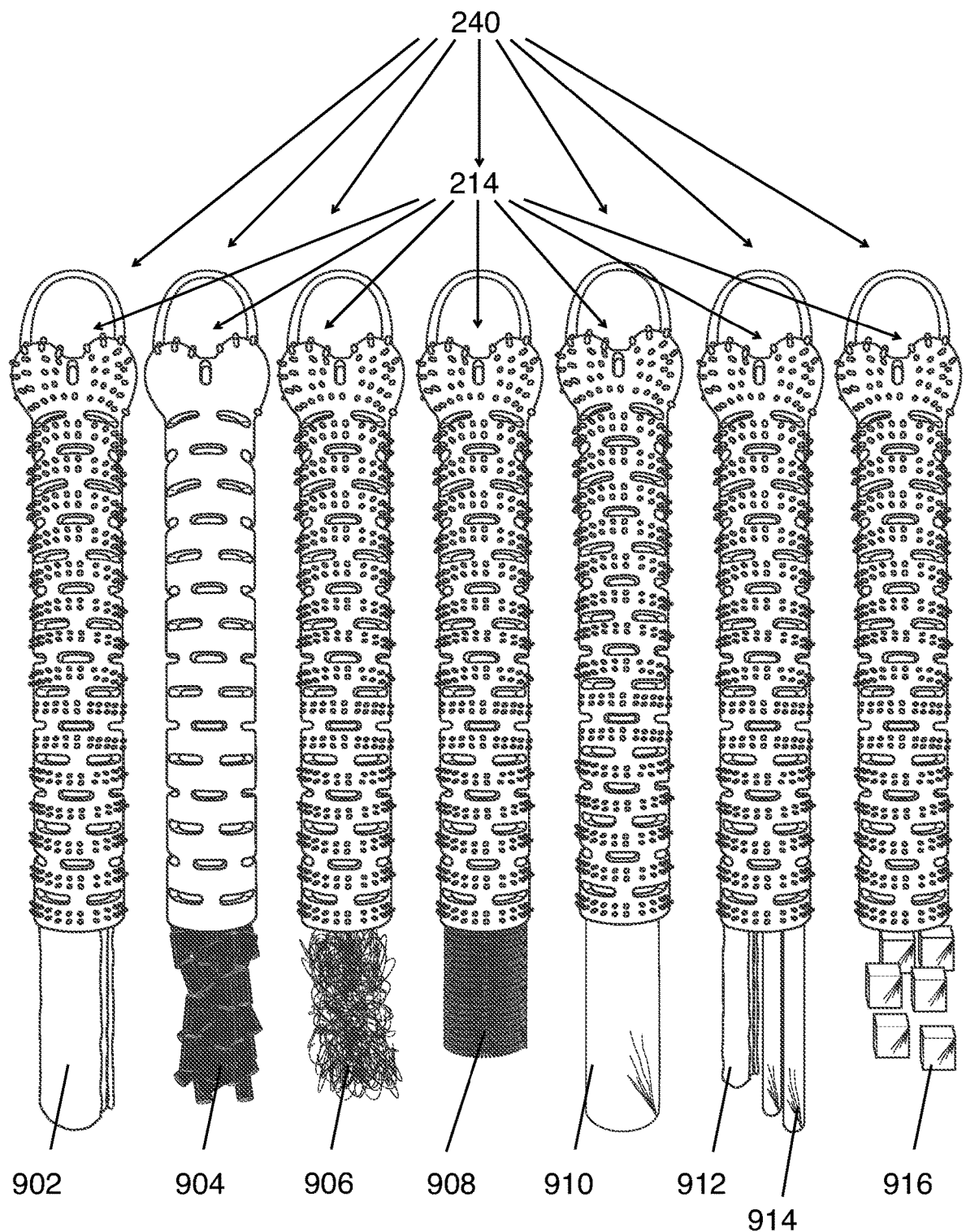
FIG. 52 shows perspective views of the attachment ends of the remainders of the devices of FIG. 25 as shown in FIG. 26, after releasably-attachable removable portions of the hollow bodies have been detached from the remainders, showing various materials that have been inserted into the interior cavities thereof.

The hollow body 206 of the device has a plurality of apertures 208 along the exterior surface 210 thereof. These apertures extend from the exterior surface 210 of the hollow body 206, through its thickness 238, to the interior cavity 202 thereof. In this embodiment, the apertures 208 are rectangular and extend transverse to the longitudinal centerline of the device 200. The apertures are dimensioned such that teeth 1000 of an animal (FIGS. 51-53) (shown as teeth models 302, 312 in FIG. 43) extend therethrough as the animal bites down on the device 200. As can be seen in FIG. 43, a portion 304, 314 of the tooth 302, 312 extends within the interior cavity 202 as the animal bites down on the device 200. The apertures 208 are also dimensioned such that the material 212 (in this case the TPE) frictionally engages an outer surface 306, 316 of the tooth 302, 312 of the animal during penetration of the aperture 308 by the tooth 302, 312. The material 212 surrounding the aperture 208 of sufficient hardness to scrape the outer surface 306, 316 of the tooth 302, 312 during frictional engagement to remove dental plaque 1003 therefrom (FIGS. 52-54).

Figure 42:
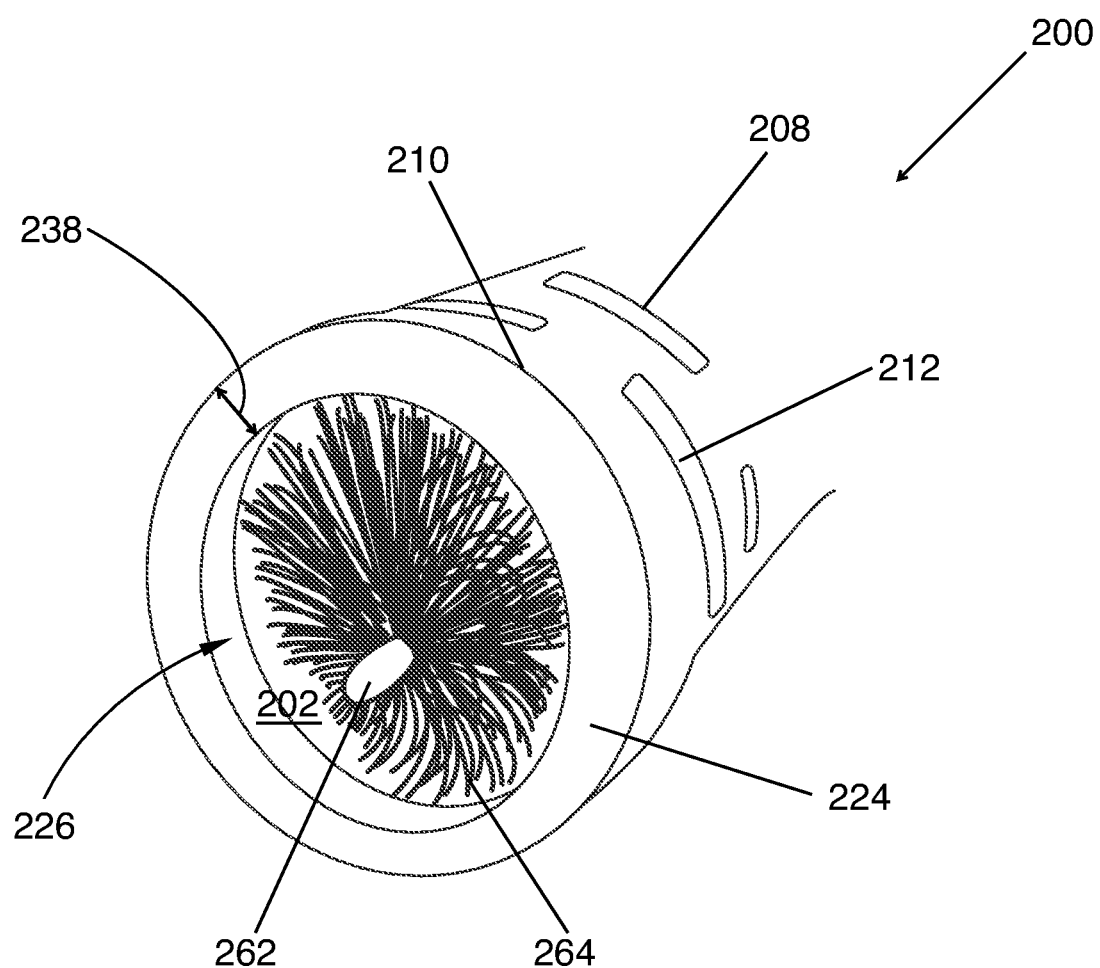
FIG. 42, shows an isometric view taken from a first end of the remainder of the device of FIG. 25 as shown in FIG. 26, after a releasably-attachable removable portion of the hollow body has been detached from the remainder; showing a brush with bristles in the interior cavity thereof.

In this embodiment, there is a brush 262 having bristles 264 within the interior cavity 202 of the device 200 (e.g., see FIG. 42). As can be best seen in FIG. 43, as the teeth 302, 312 extend into the interior cavity 202 of the device 200, the outer surface 306, 316 of the portion thereof 304, 314 extending into the interior cavity 202 comes into contact with the bristles 264 of the brush 262 and is cleaned thereby.

Figure 53:
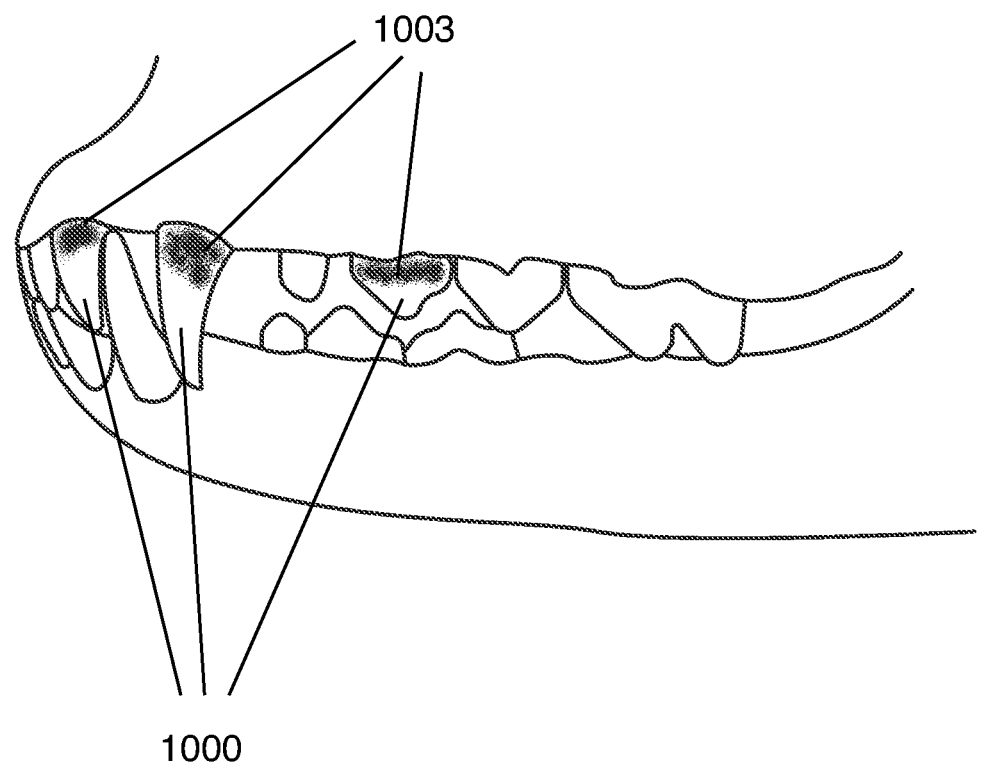
FIG. 53 schematically shows teeth of a large dog before having chewed a device of the present technology.
Figure 54:
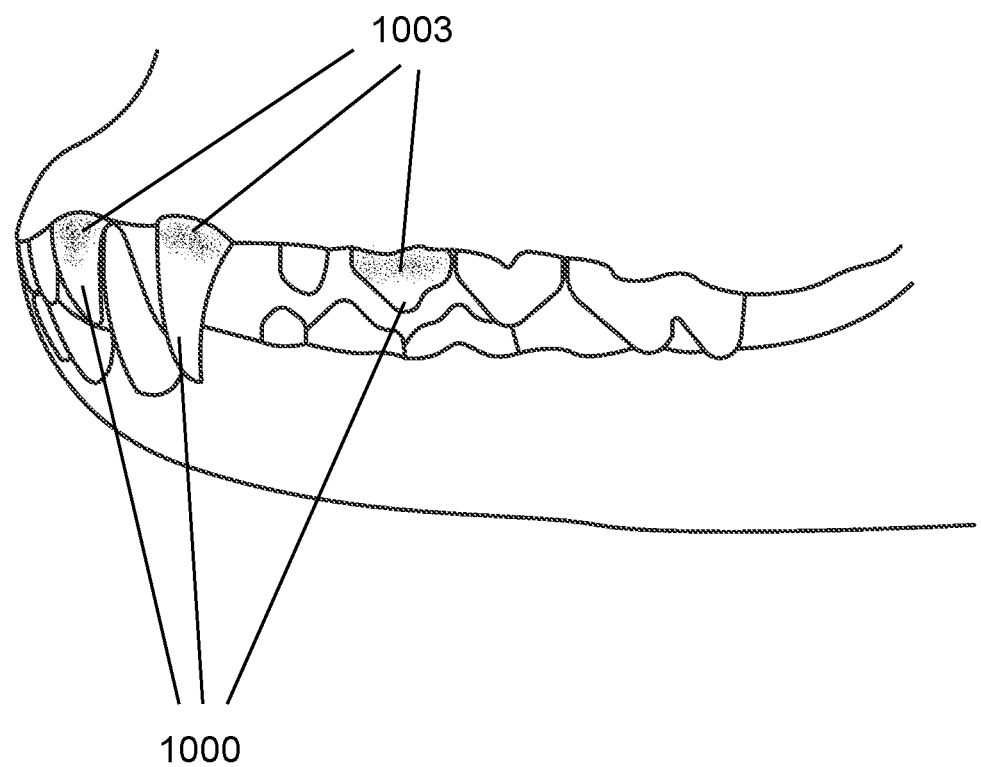
FIG. 54 schematically shows the same teeth of the same dog of FIG. 53 after having chewed on a device of the present technology for two days.
Figure 55:
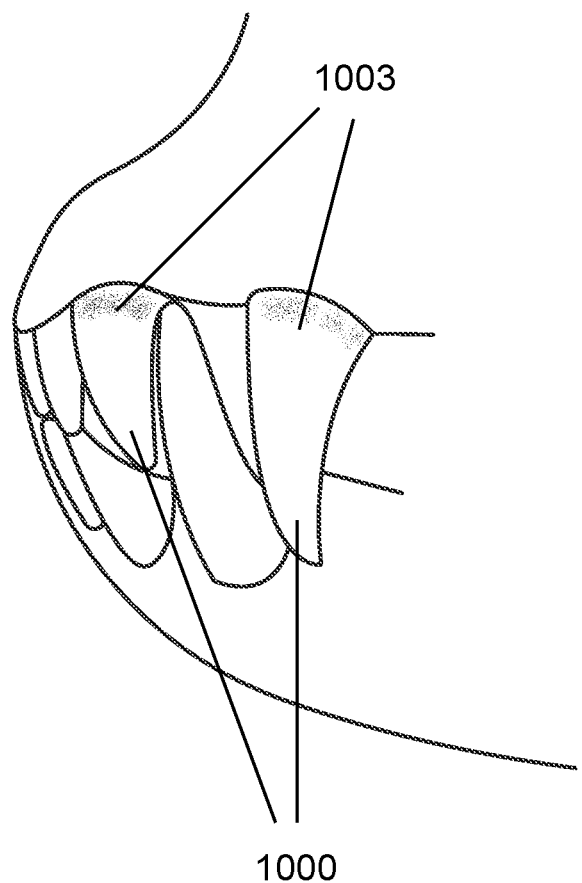
FIG. 55 schematically shows a close-up view of the same teeth of the same dog of FIG. 53 after having chewed on a device of the present technology for three days.

The effectiveness of the device 200 can be seen in FIGS. 53, 54, and 55. In FIG. 53, the dog has patches of tartar 1003 that can be seen on its teeth 1000. (The tartar 1003 can be more easily seen with a dental stain designed for that purpose.) In FIG. 54, after two days of using (at the dog's discretion) the device 200, it can be seen that the size of the tartar 1003 has been greatly reduced. In FIG. 55, after three days of using (at the dog's discretion) the device 200, it can be seen that the size of the tartar 1003 is even further reduced.

Figure 25:
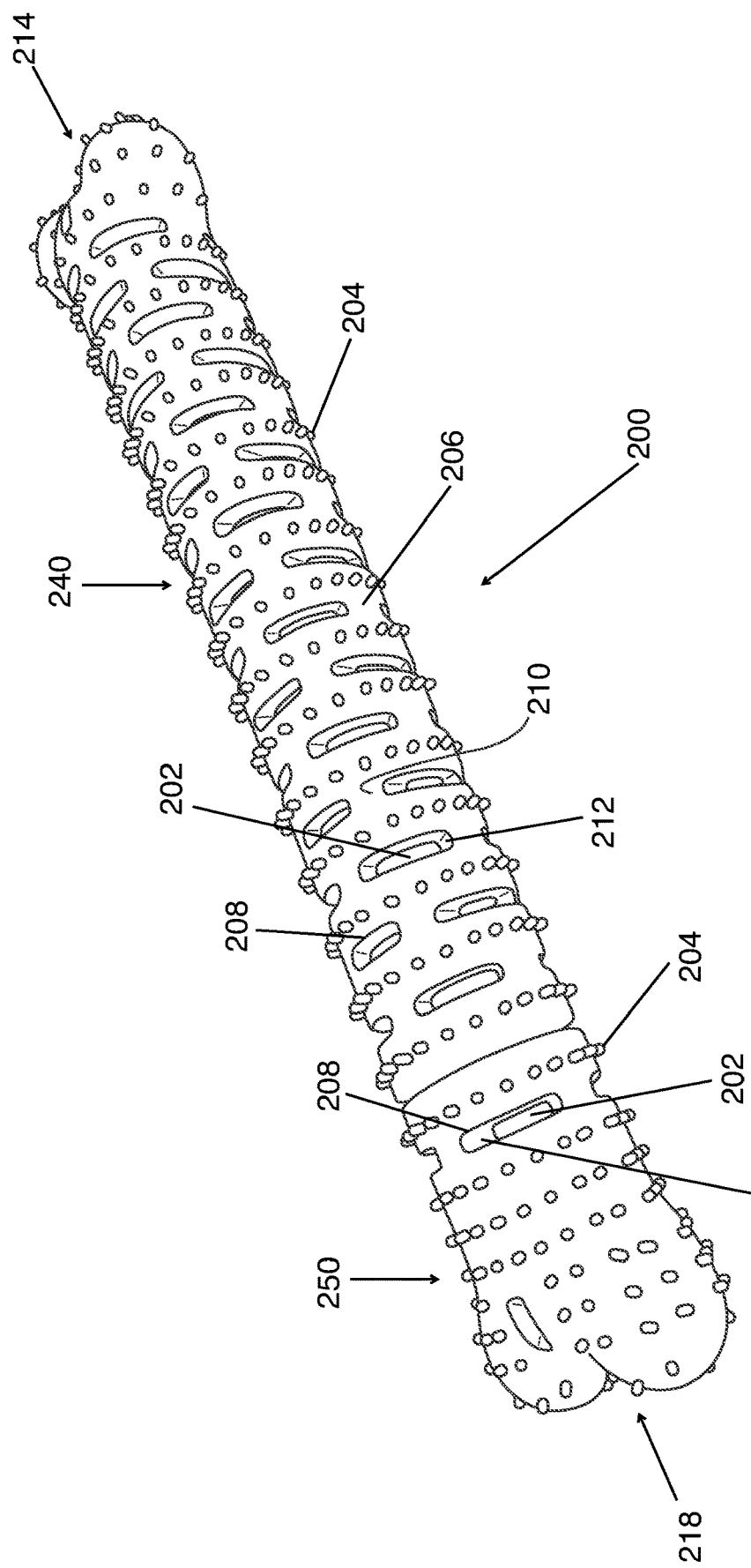
FIG. 25 shows an isometric view taken from a first end of an animal dental hygienic device being a seventeenth embodiment of the present technology, being dog-bone shaped.
Figure 26:
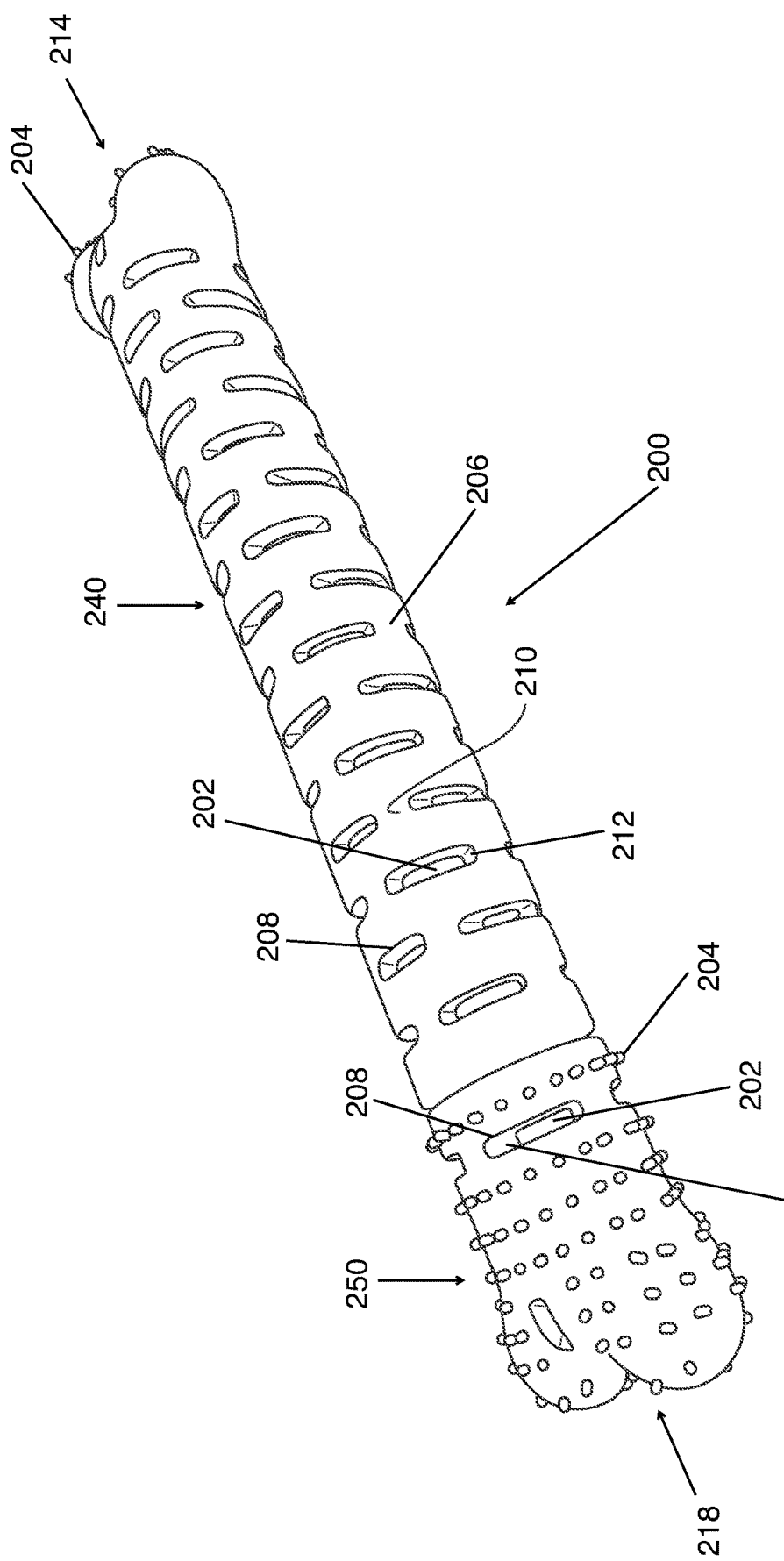
FIG. 26 shows an isometric view taken from a first end of the device of FIG. 25 with some of the projections having been removed for clarity.
Figure 27:
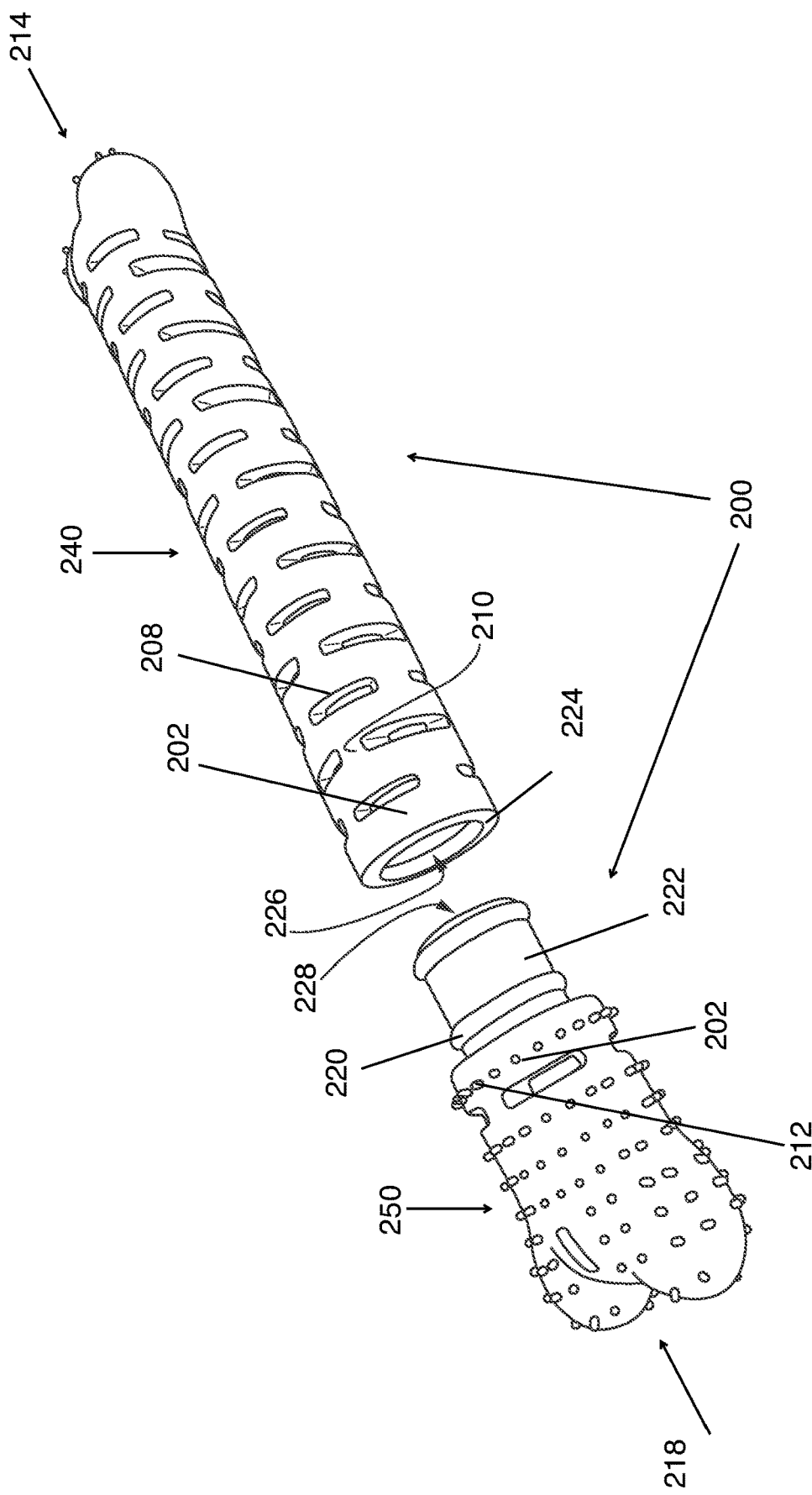
FIG. 27 shows an isometric view taken from a first end of the device of FIG. 25 as shown in FIG. 26, wherein a releasably-attachable removable portion of the hollow body has been detached from the remainder of the hollow body.
Figure 28:
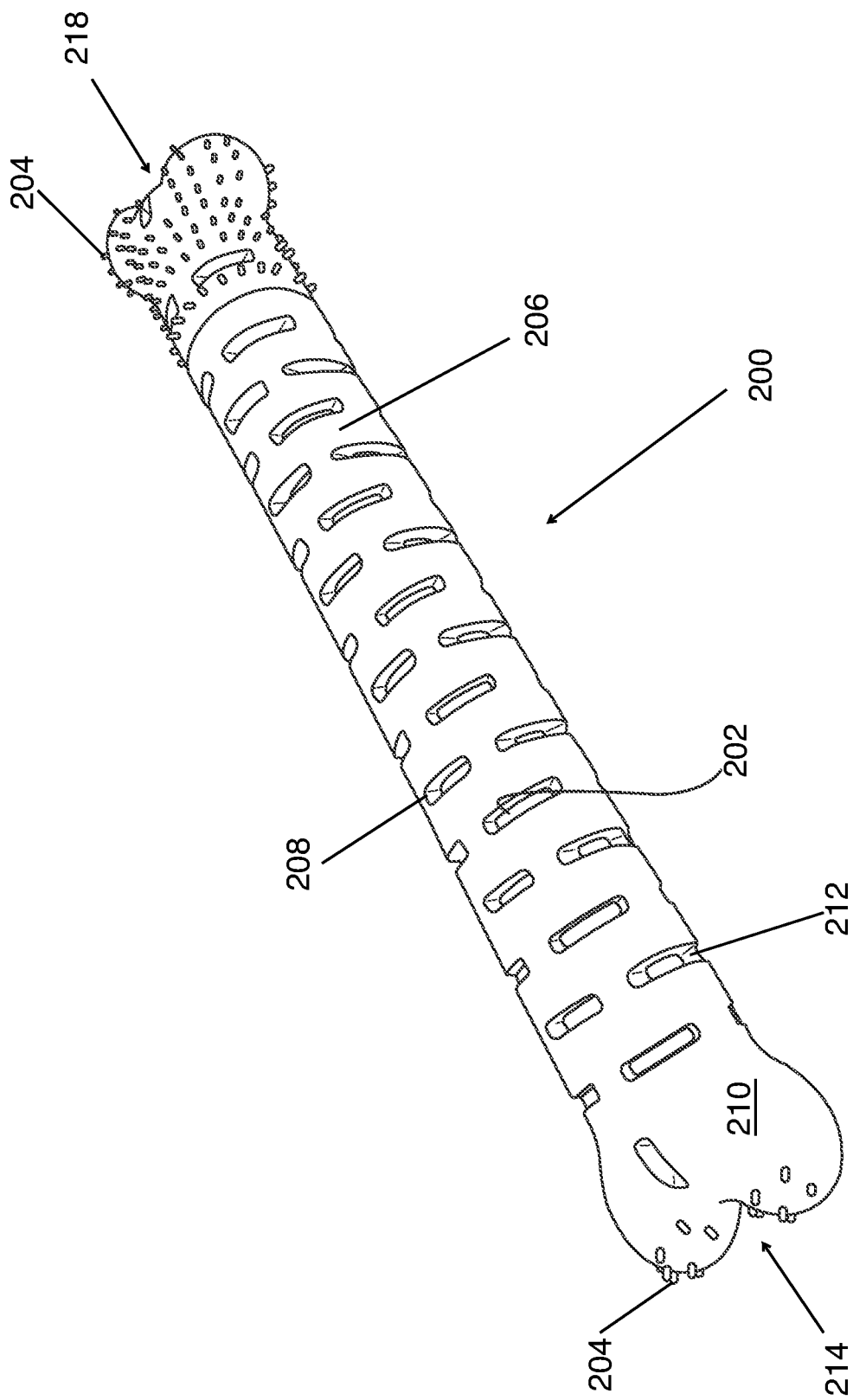
FIG. 28 shows an isometric view taken from a second end of the device of FIG. 25 as shown in FIG. 26.
Figure 29:
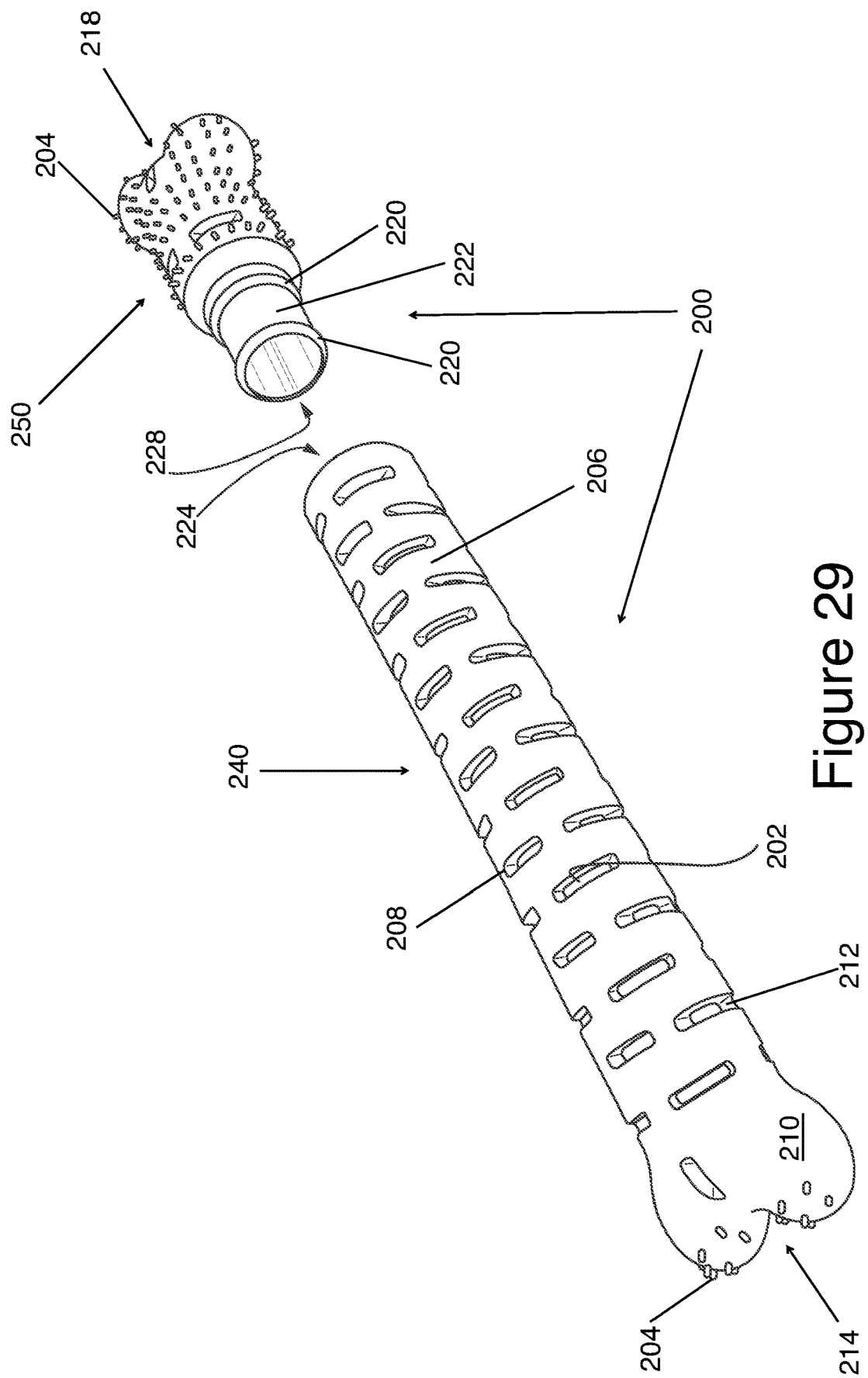
FIG. 29 shows an isometric view taken from a second end of the device of FIG. 25 as shown in FIG. 26, wherein a releasably-attachable removable portion of the hollow body has been detached from the remainder of the hollow body.
Figure 30:
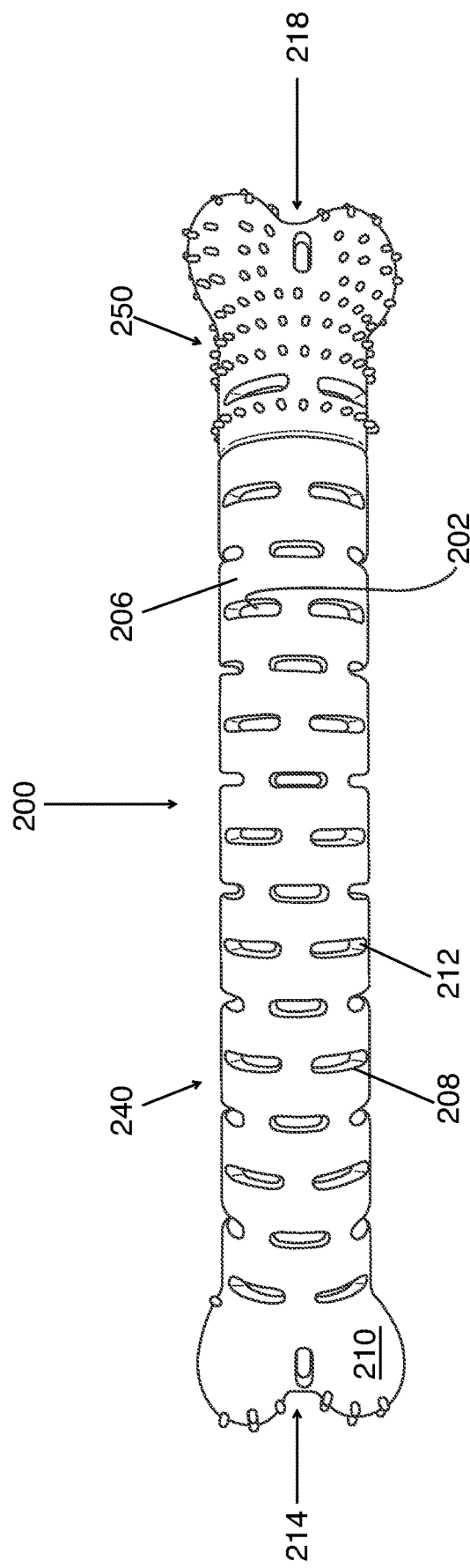
FIG. 30 shows a side elevation view of the device of FIG. 25 as shown in FIG. 26.
Figure 31:
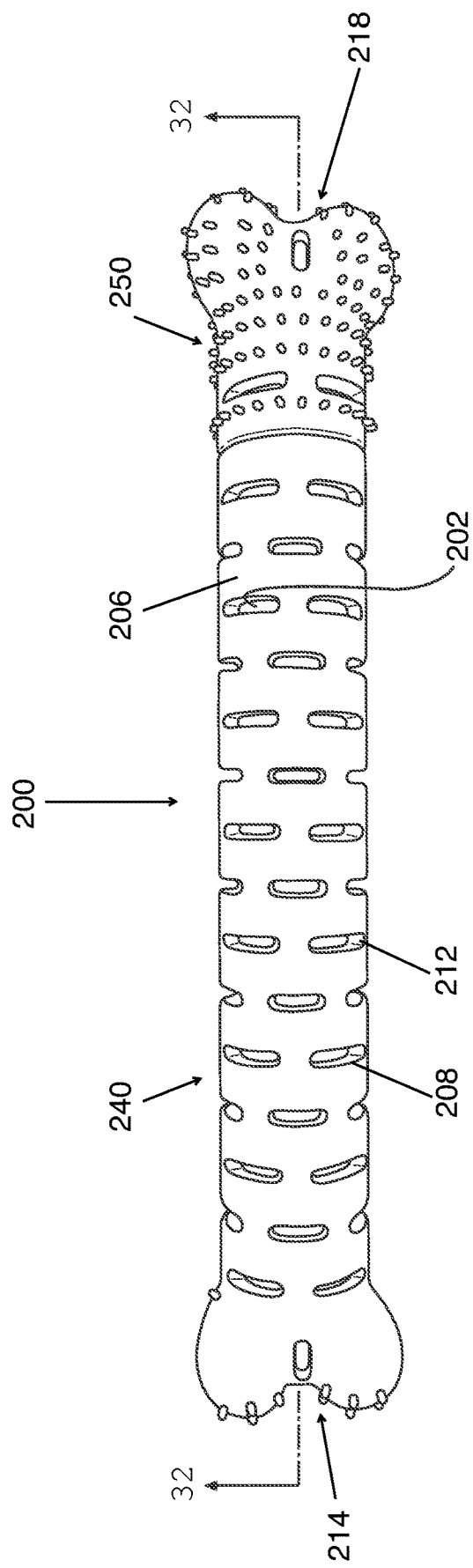
FIG. 31 shows a side elevation view of the device of FIG. 25 as shown in FIG. 26 illustrating cross-section line 32-32.
Figure 32:
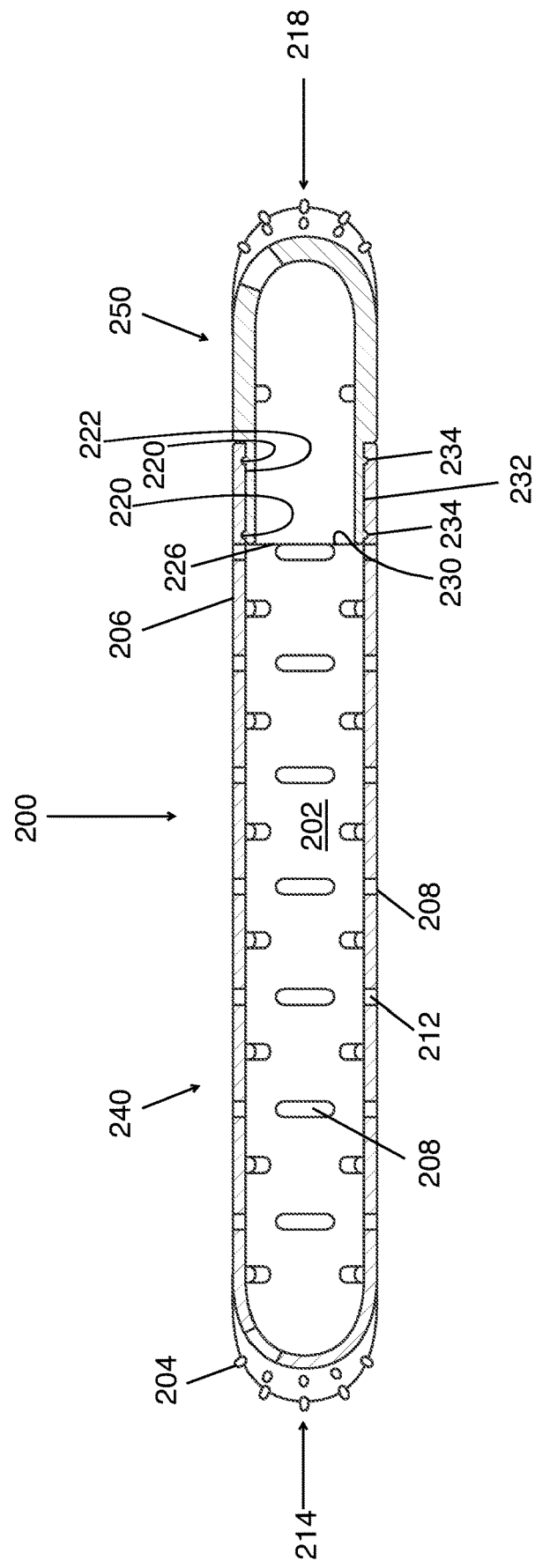
FIG. 32 shows a cross section of the device of FIG. 25 as shown in FIG. 26 taken along the line 32-32 in FIG. 31.
Figure 33:
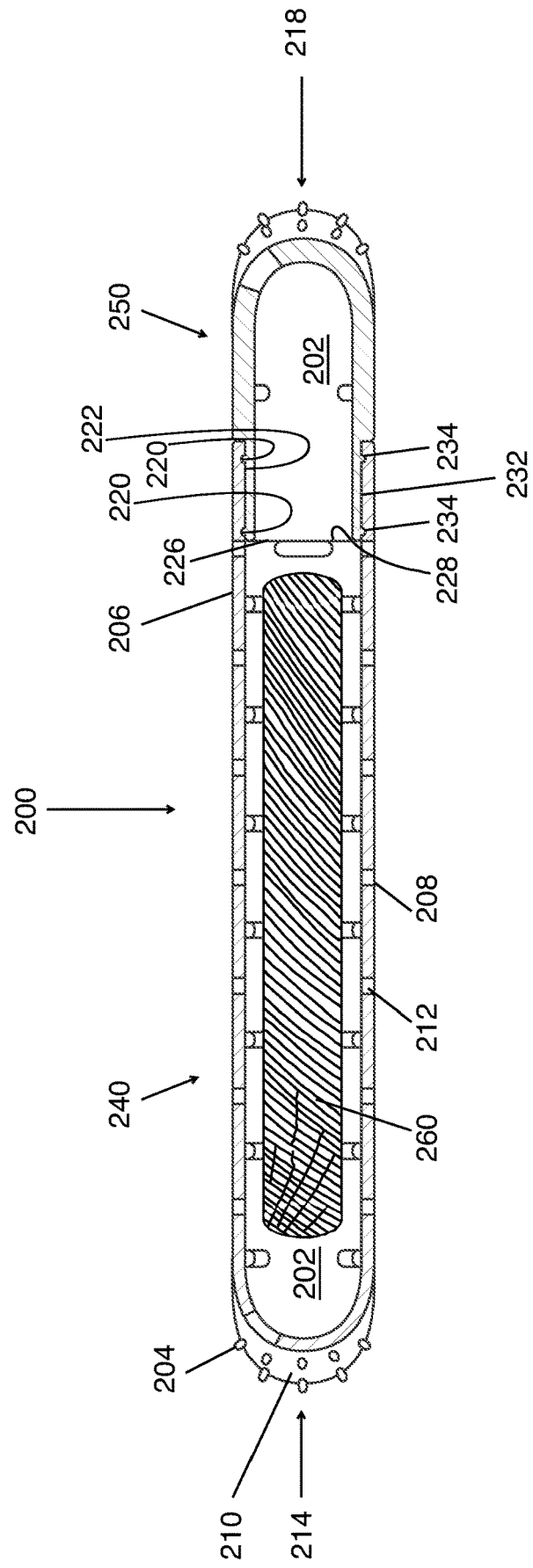
FIG. 33 shows the cross section of FIG. 32 with a piece of wood shown schematically in the interior cavity of the device.
Figure 34:
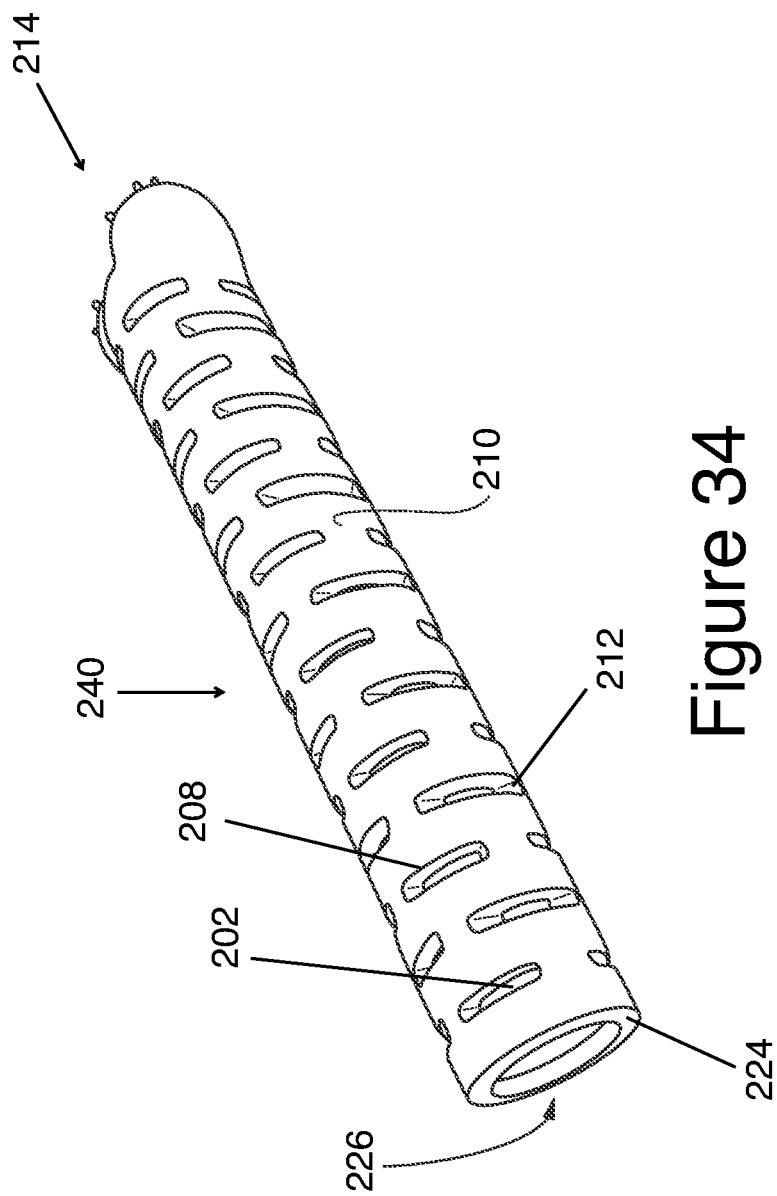
FIG. 34 shows an isometric view of the attachment end of the remainder of the device of FIG. 25 as shown in FIG. 26, after a releasably-attachable removable portion of the hollow body has been detached from the remainder.
Figure 44:
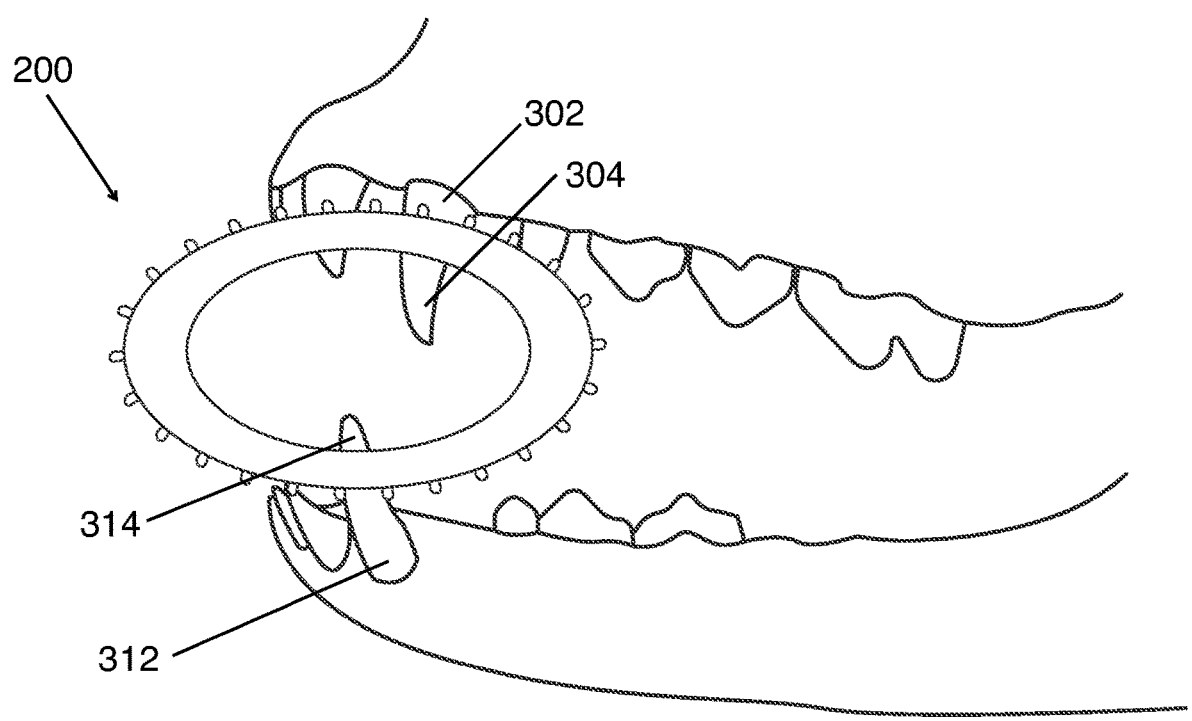
FIG. 44 is an elevation view of the attachment end of the remainder of the device of FIG. 25 as shown in FIG. 26, after a releasably-attachable removable portion of the hollow body has been detached from the remainder, showing teeth of a dog penetrating the device, with the mouth of the animal almost closed.

As can be seen in FIG. 25, many projections 204 extend from the exterior surface 210 of the hollow body 206. In this embodiment, these projections 204 are made from the same material as the hollow body 206 itself. In this embodiment, these projections 204 are positioned, dimensioned, shaped and structured to massage the gums of the dog as the dog bites the device 200 and its teeth 302, 312 have deeply penetrated the apertures 208. This may help to clean the animal's gums, as can be seen in a comparison of FIGS. 53, 54, and 55. The hollow body 206 is flexible as the animal bites the device 200. In FIG. 42 the device is annular in cross section. In FIG. 43 the device 200 has become slightly oval in cross section. In FIG. 44 the device 200 has become a much more pronounced oval in cross section. This flexibility will cause the projections 204 to move with respect to the mouth and teeth of the animal and may assist in enhancing the cleaning action of the device 200.

Figure 35:
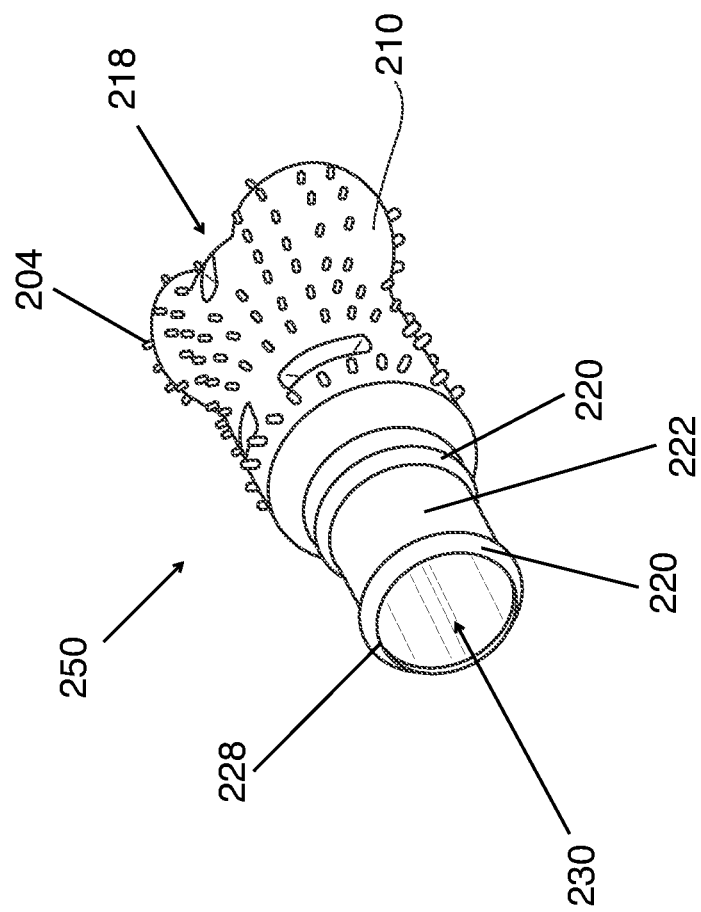
FIG. 35 shows an isometric view of the removable portion of the device of FIG. 25 as shown in FIG. 26.
Figure 36:
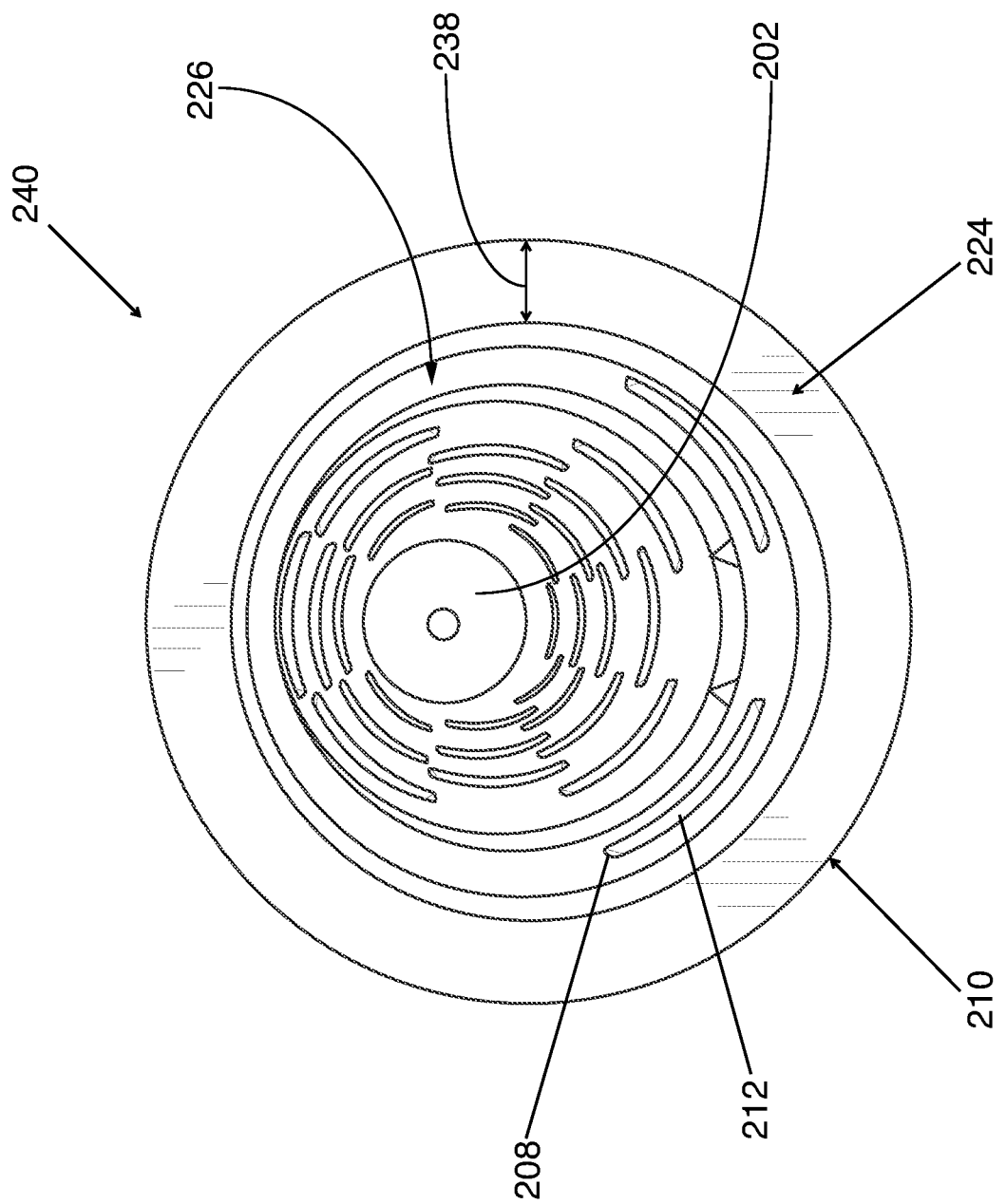
FIG. 36 shows an elevation view of the attachment end of the remainder of the device of FIG. 25 as shown in FIG. 26, after a releasably-attachable removable portion of the hollow body has been detached from the remainder.
Figure 37:
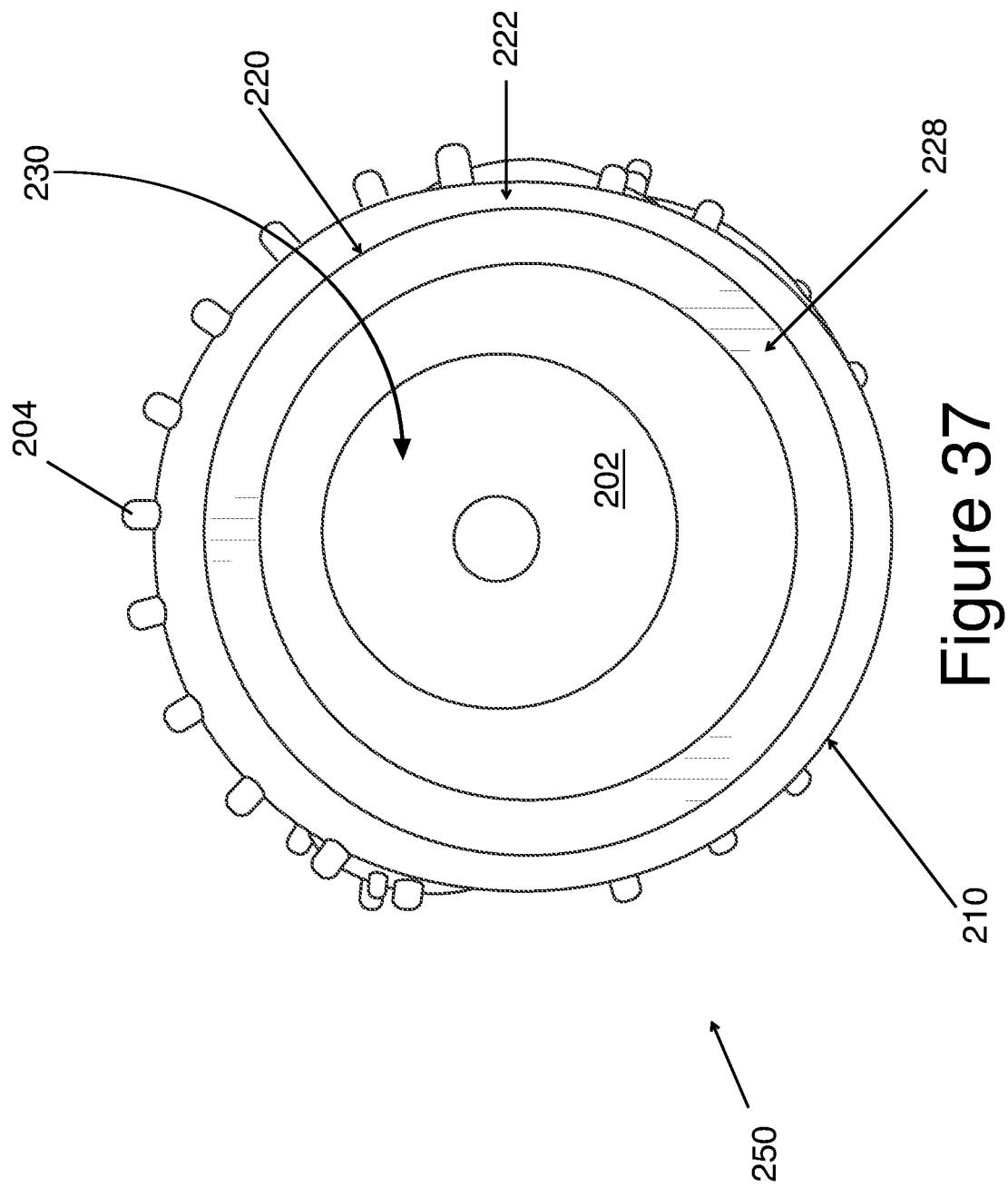
FIG. 37 shows an elevation view of the attachment end of the removable portion of the device of FIG. 25 as shown in FIG. 26.
Figure 38:
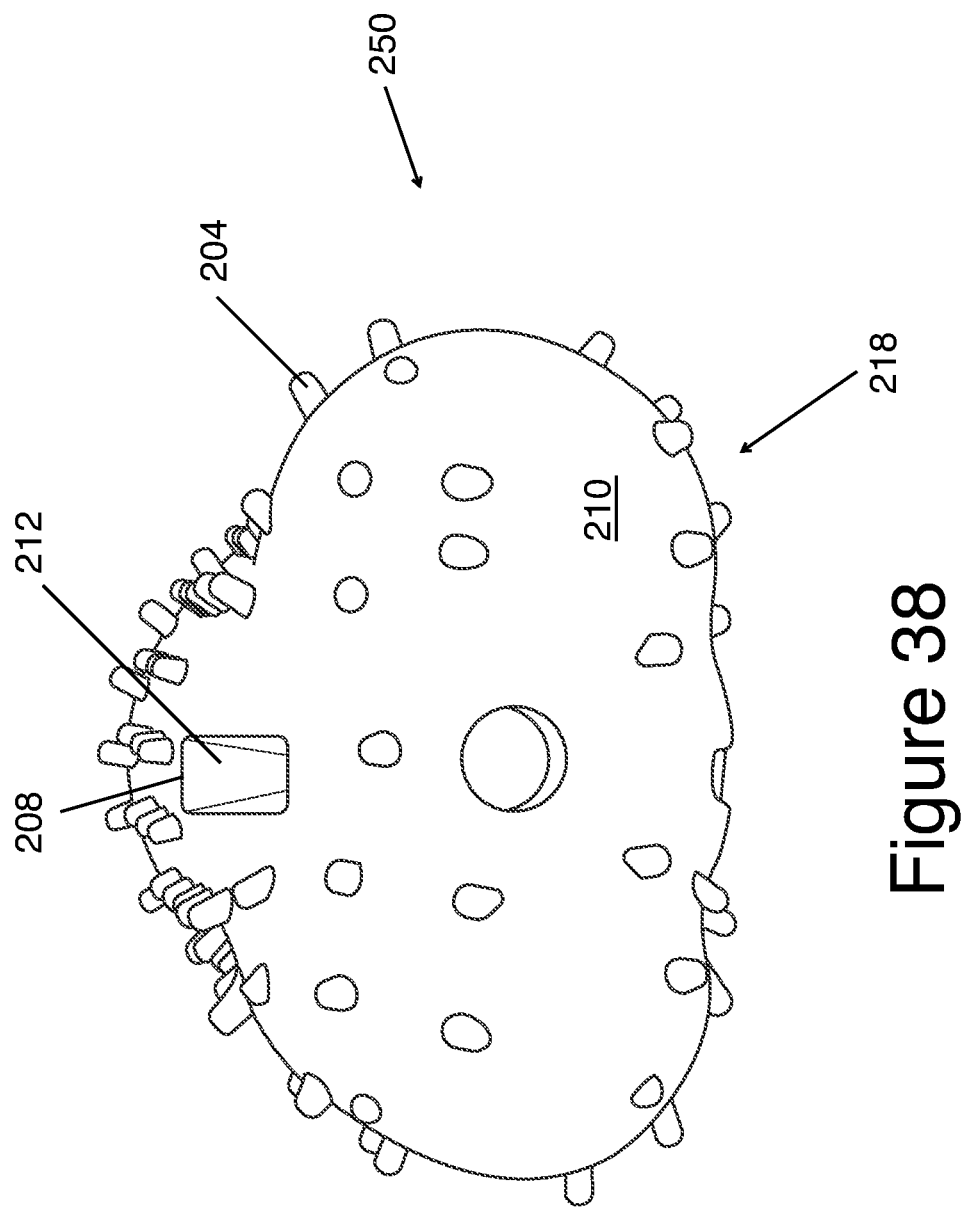
FIG. 38 shows an elevation view of the non-attachment end of the removable portion of the device of FIG. 25 as shown in FIG. 26.
Figure 39:
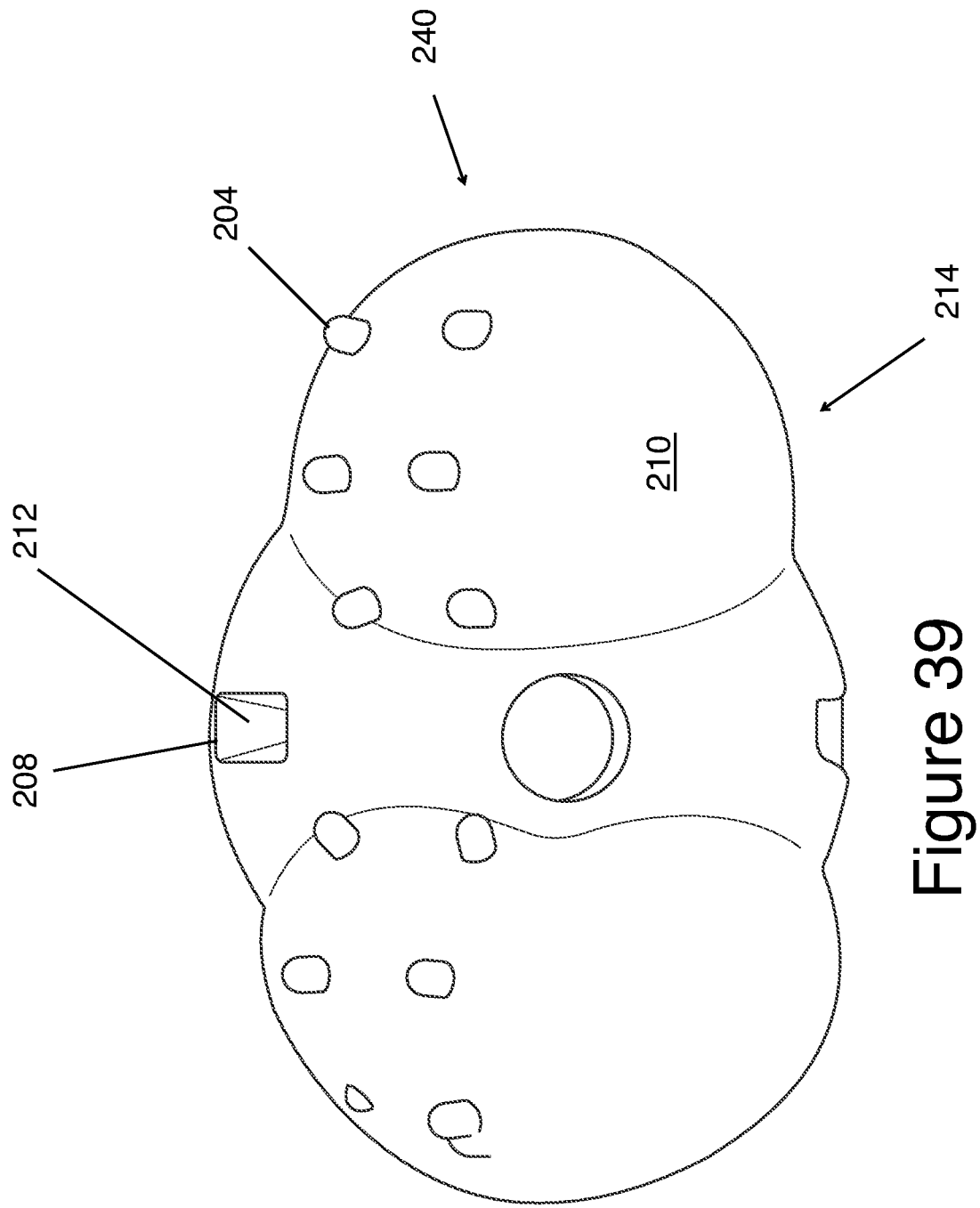
FIG. 39 shows an elevation view of the non-attachment end of the remainder of the device of FIG. 25 as shown in FIG. 26, after a releasably-attachable removable portion of the hollow body has been detached from the remainder.
Figure 40:
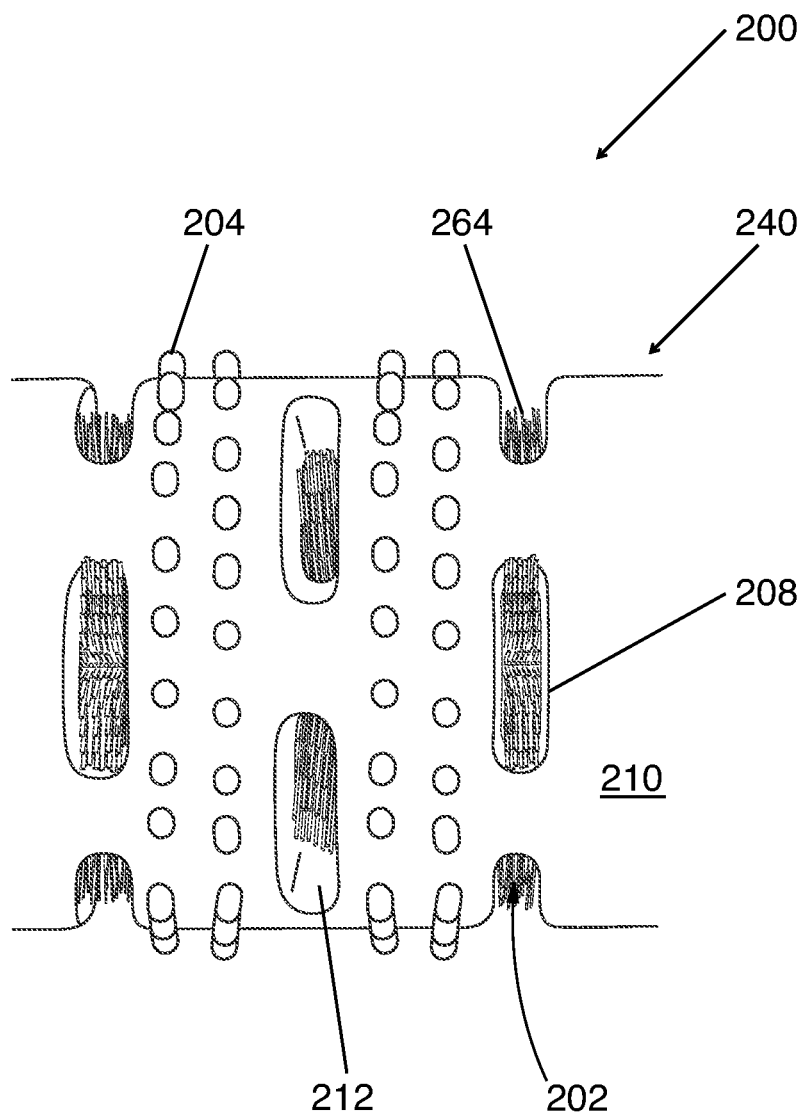
FIG. 40 is a close-up elevation view of the side of the hollow body of the device of FIG. 25, showing a brush with bristles in the interior cavity thereof.
Figure 41:
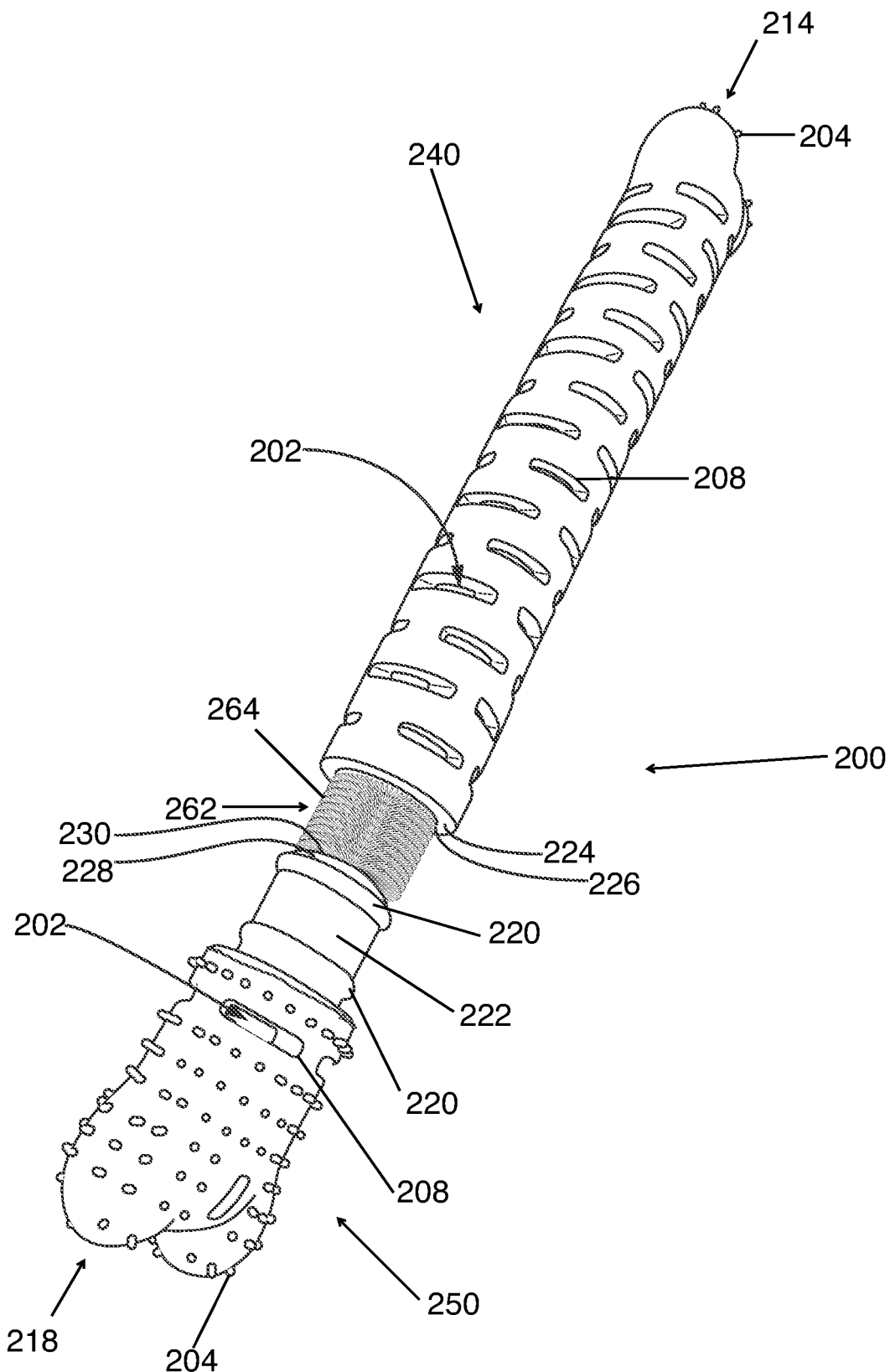
FIG. 41 is a top, side perspective view taken from a first end of the device of FIG. 25, with the removable portion detached from the remainder, showing a brush with bristles in the interior cavity thereof.

In this embodiment, the device 200 has a releasably-attached removable portion 250 (which can be best seen in FIG. 35). When the removable portion 250 is detached from the remainder 240 of the device 200, the interior cavity 202 thereof is accessible. This allows for structures (such as brush 262) to be removed from and/or placed into the interior cavity 202. Referring to FIG. 52, there are shown (a non-limiting set of) examples of materials that can be placed within the interior cavity 202 of the device 200: (I) A rawhide stick 902 can be placed within the interior cavity 202 for increasing the attractiveness of the device 200 to dogs. (II) Metallic coils 904 can be placed within the interior cavity 202 for increasing the teeth cleaning capability of the device 200. (III) Plastic strands 906 can be placed within the interior cavity 202 for increasing the teeth cleaning capability of the device 200. (IV) A brush having bristles 908 can be placed within the interior cavity 202 for increasing the teeth cleaning capability of the device 200. (V) A wooden rod 910 can be placed within the interior cavity 202 for increasing the attractiveness of the device 200 to dogs. (See also FIG. 33.) (VI) A rawhide stick 912 and wooden rods 914 can be placed within the interior cavity 202 together for increasing the attractiveness of the device 200 to dogs. (VII) Wooden cubes 916 can be placed within the interior cavity 202 for increasing the attractiveness of the device 200 to dogs.

Referring to FIGS. 35 to 41, in this embodiment, the releasably-attached removable portion 250 is one 218 of the flared ends 214, 218 of the device 200. In this respect, the removable portion 250 has a plug 216, the end 228 of which fits securely inside the end 224 of the reminder 250 of the device 200. The plug 216 has a cylindrical portion 222 with raised flanges 220 that can be inserted into the end 224 of the remainder 240. Once inside the end 224 of the remainder 240, the raised flanges 220 fit snugly within grooves 234 and the cylindrical portion 222 mates with an interior cylindrical portion 232 of the interior of the end 224 of the remainder 240. This registration and mating relationship is such that the removable portion 250 will not generally become detached from the remainder 240 during normal use by a dog, but a human can pull the removable portion 250 apart from the remainder 240. Once removed, the end 228 of the removable portion 250 has a hole 230 through which the interior cavity 202 of the hollow body 206 can be accessed. Further, once the removable portion 250 is removed, the end 224 of the remainder 240 has a hole 226 through which the interior cavity 202 can be accessed.

Figure 45:
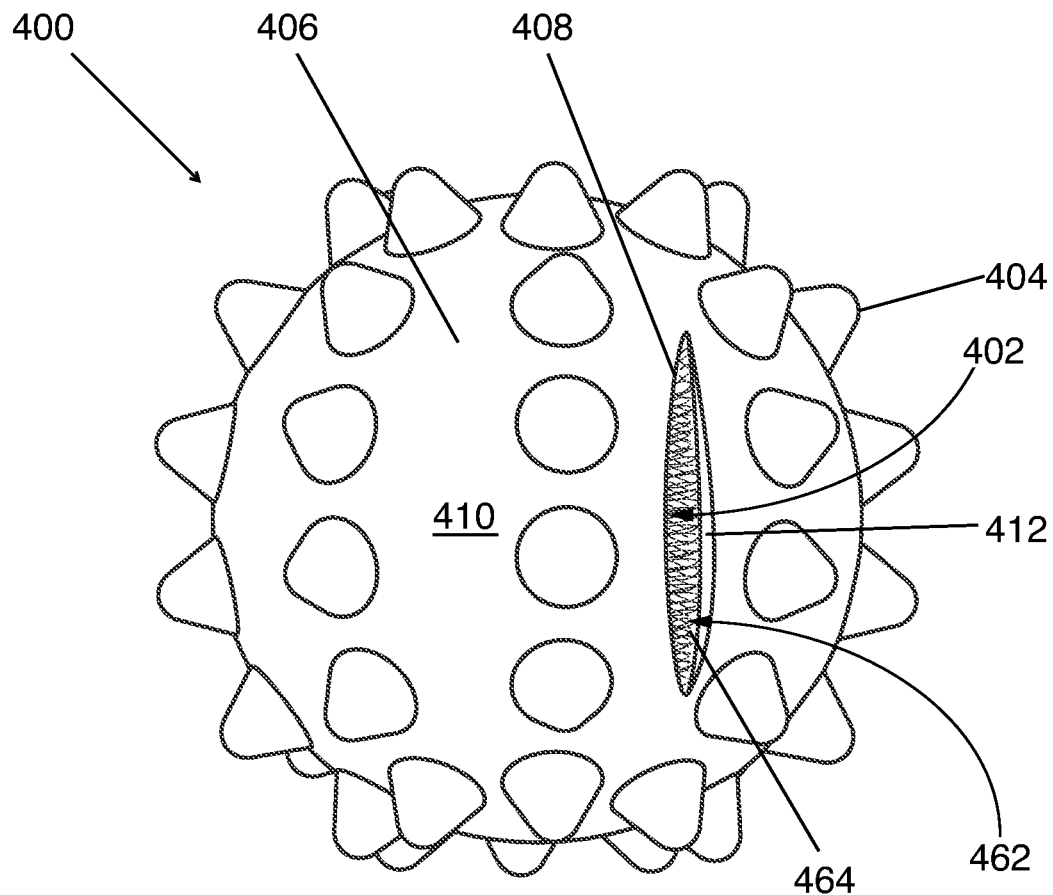
FIG. 45 shows an isometric view of an animal dental hygienic device being a nineteenth embodiment of the present technology, being shaped as a sphere.
Figure 46:
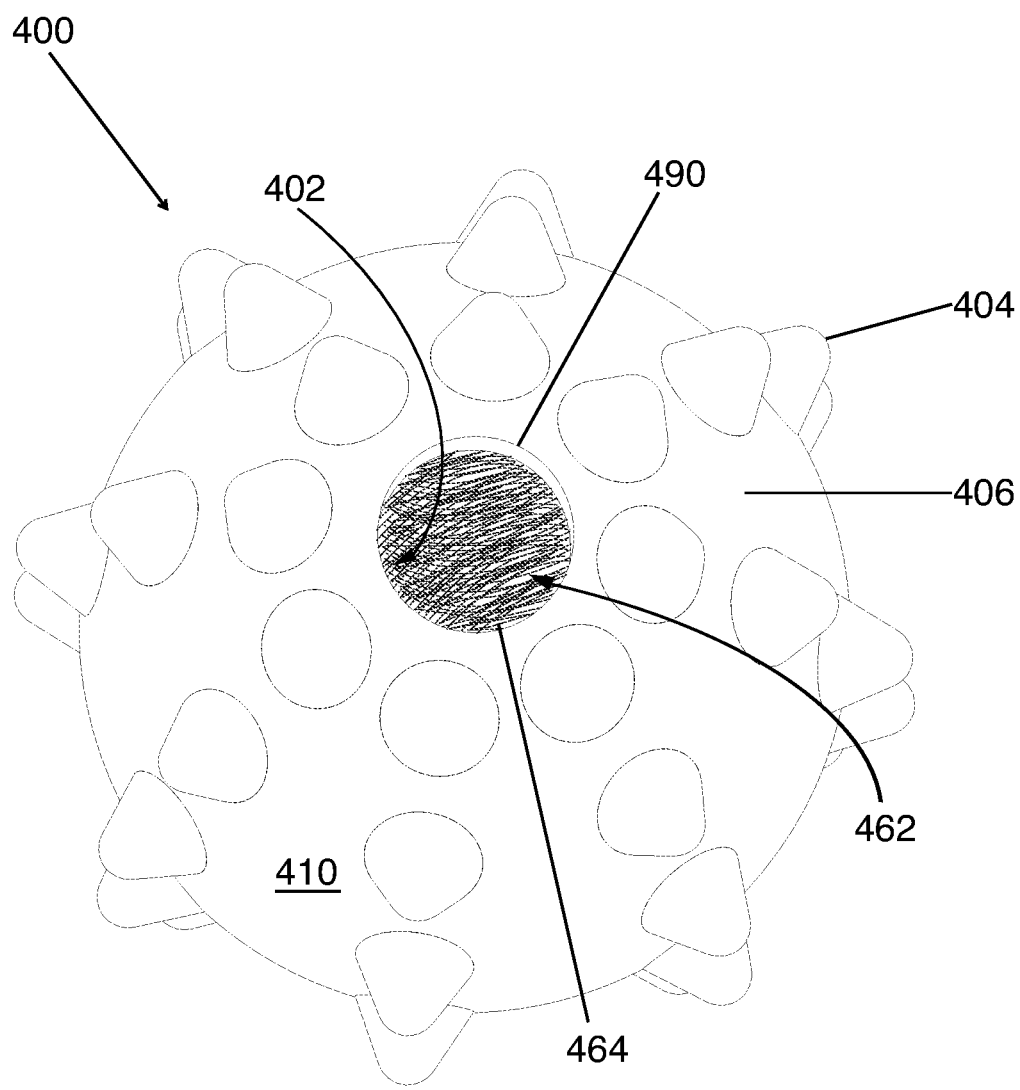
FIG. 46 shows a side elevation view of the device of FIG. 45 with a releasably-attachable removable portion of the hollow body removed.
Figure 47:
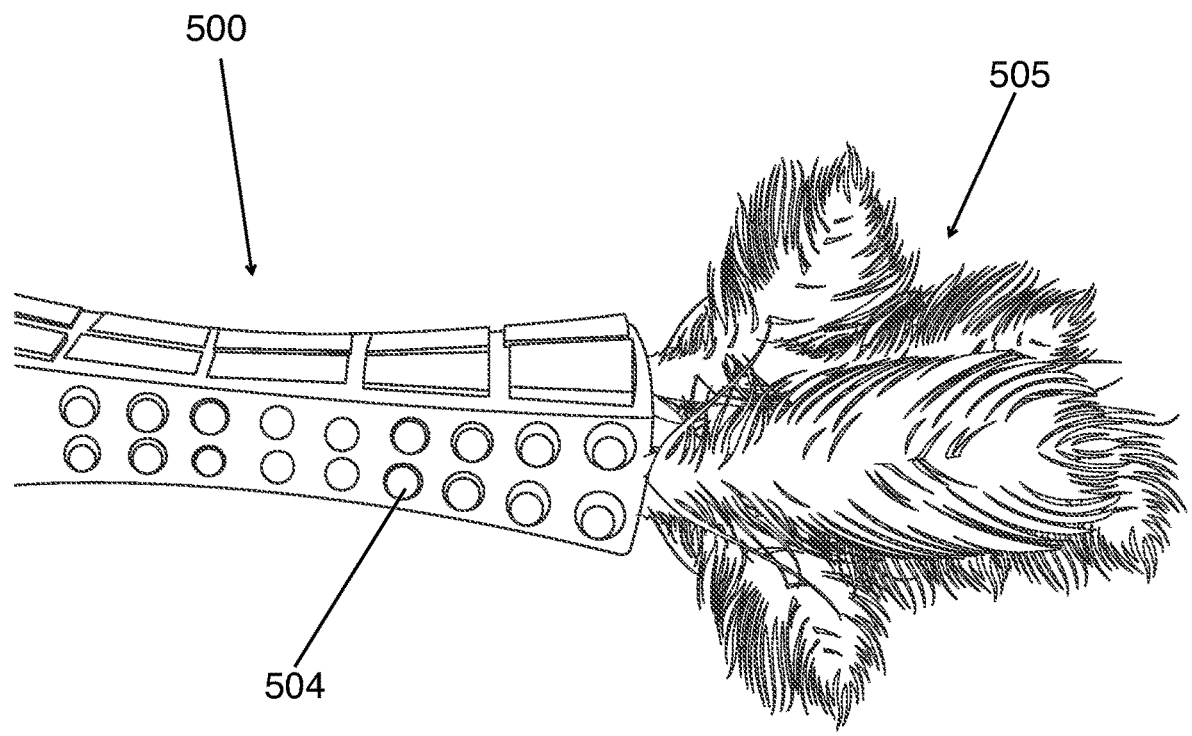
FIG. 47 shows an elevation view of an animal dental hygienic device being a twentieth embodiment of the present technology, being shaped and sized as a part of a cat toy.
Figure 48:
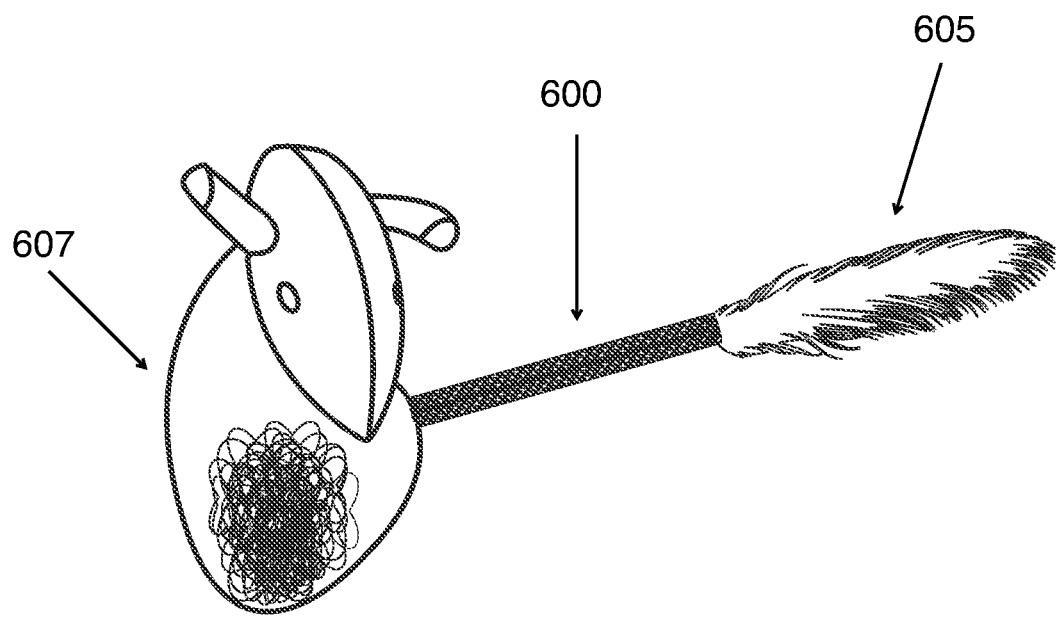
FIG. 48 shows a perspective view of an animal dental hygienic device being an twenty-first embodiment of the present technology, being shaped and sized as a part of a cat toy.
Figure 49:
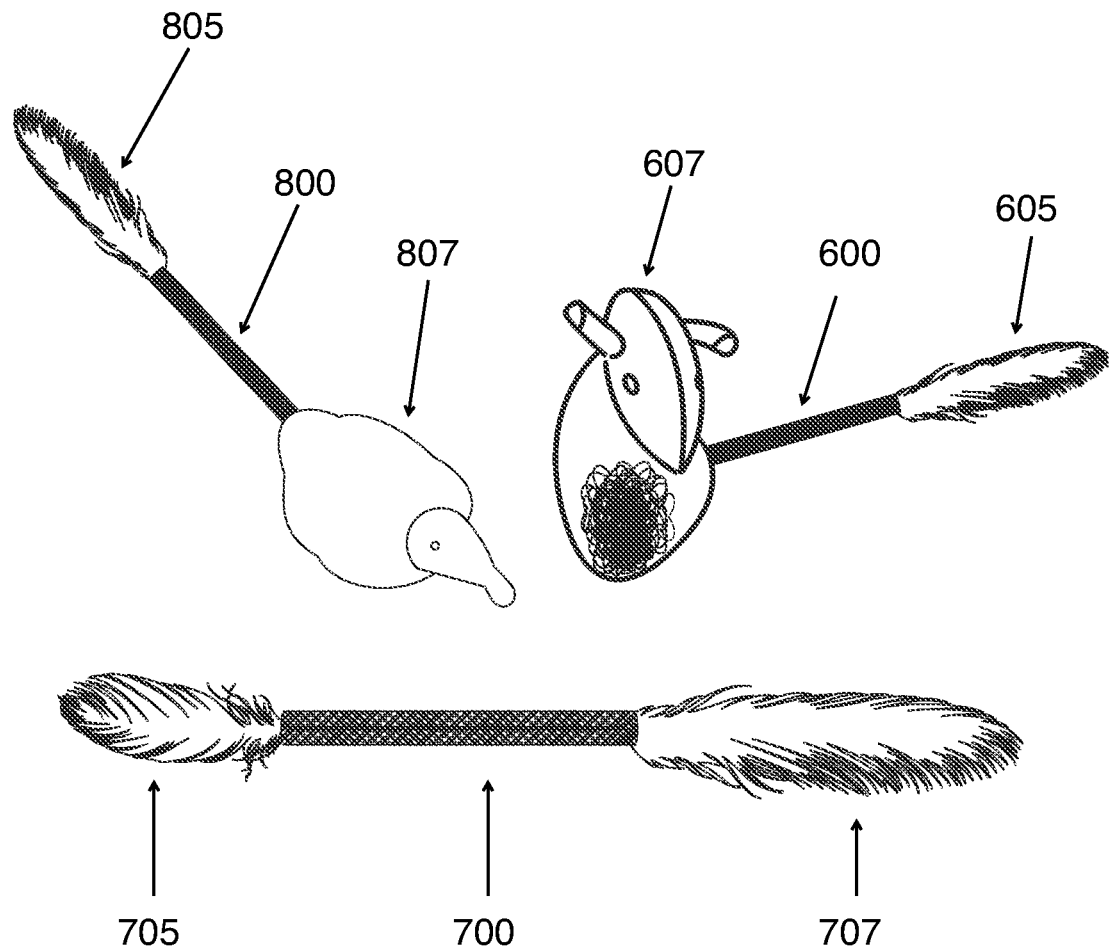
FIG. 49 shows a perspective view of the device of FIG. 48 along with two other animal dental hygienic devices being the twenty-second and twenty-third embodiments of the present technology, being shaped and sized as a parts of a cat toys.
Figure 50:
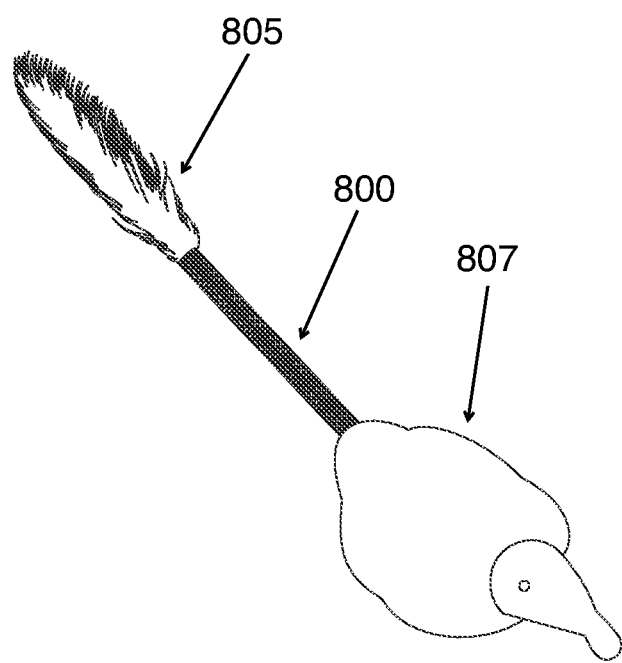
FIG. 50 is a side elevation view of a device shown in FIG. 49 being the twenty-second embodiment of the present technology.
Figure 51:
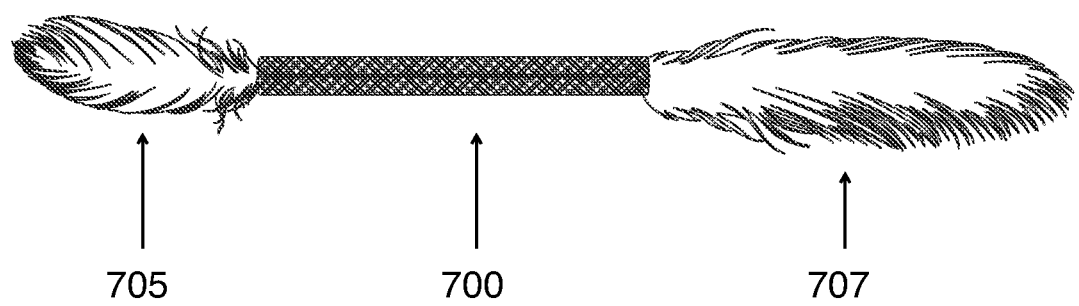
FIG. 51 is a side elevation view of a device shown in FIG. 49 being the twenty-third embodiment of the present technology.

Referring to FIGS. 45 and 46, there is shown an embodiment of the present technology being an animal dental hygienic device 400 that is a sphere in shape. The device 400 has a hollow body 406 having an exterior surface 410 and an interior cavity 402 therein. Extending from the exterior surface 410 are a plurality of projections 404. A plurality of apertures 408 are present in the hollow body 406 extending from the exterior surface 410 thereof to the interior cavity 402 thereof, the material 412 surrounding the aperture 408 of sufficient hardness to scrape the outer surface of a tooth during frictional engagement to remove dental plaque therefrom. There is a brush 462 having bristles 464 in the interior cavity 402 of the device 400. The device has a releasably-attached removable portion (not shown), which, when removed, provides an opening 490 through which the interior cavity 402 is accessible. Material can be removed from and placed into the interior cavity 402 of the device 400 via the opening 490. As the functionality of the various components of the device 400 is the same as was previously described in relation to device 200, it will not be repeated.

Referring to FIGS. 47, 48, 49 and 50, various embodiments of the present technology being animal dental hygienic devices 500, 600, 700, 800 (being dimensioned and structured for domestic cats), which are attached to various cat toys 505, 605/607, 705/707, 805/807 (respectively) are shown. The device 500 has projections 504. As the functionality of the various components of the devices 500, 600, 700, 800 is the same as was previously described in relation to device 200, it will not be repeated.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A dental hygienic device for independent use by a dog, comprising:
   a hollow body formed in the shape of a tube having a longitudinal centerline, the hollow body having an exterior surface and an interior cavity, the hollow body being sized to fit transversely relative to the longitudinal centerline within the mouth of the dog and to be bitten by the dog;
   a brush having radially disposed bristles, the brush located within the interior cavity of the hollow body, the bristles providing partial engagement with a tooth of the dog upon the hollow body being bitten by the dog;

the hollow body having a plurality of radially discontinuous bounded apertures evenly positioned and interspersed around the exterior surface of the hollow body, the apertures arranged in longitudinally displaced sets along the hollow body, each set being radially offset from an adjacent set, and every other set being longitudinally aligned, the hollow body deformable under pressure exerted by the dog biting the hollow body:

while in an undeformed state, the apertures each comprise a shape of a rectangle, each rectangle having a length extending across the exterior surface transverse to the longitudinal centerline of the hollow body, and each rectangle forming open channels extending through the hollow body from the exterior surface to the interior cavity;

while in a deformed state upon insertion of the tooth of the dog, at least one of the apertures comprises dental-hygienically active dimensions allowing the tooth of the dog to penetrate through a respective one of the open channels such that a material of the aperture is of sufficient hardness to scrape an outer surface of the tooth of the dog and frictionally engages the outer surface of the tooth of the dog during penetration of the aperture by the tooth, the material surrounding the aperture scraping the outer surface of the tooth during frictional engagement to remove dental plaque, and such that a portion of the tooth of the dog extends within the interior cavity during penetration of the aperture by the tooth;

wherein the hollow body has at least one releasably-attachable removable portion allowing access to place the brush in the interior cavity, the releasably-attachable removable portion being configured to be bitten by the dog, and wherein at least a portion of the releasably-attachable removable portion is configured to be received in the hollow body and to securingly engage an inner wall of the hollow body, and wherein projections extend outwardly from the exterior surface of the hollow body, the projections being positioned in a series of two circumferential rows interspersed around the hollow body, each series of the two circumferential rows being located between one ring of the plurality of radially discontinuous bounded apertures, the projections being uniformly dimensioned, shaped and structured to be dental-hygienically active as the dog bites the hollow body.

2. The dental hygienic device for independent use by a dog of claim 1, wherein the projections are adapted for frictionally engaging at least one of the outer surface of the tooth of the dog and gums of the dog as the tooth of the dog penetrates a one of the plurality of apertures.

3. The dental hygienic device for independent use by a dog of claim 1, wherein the device is dog-bone shaped.

4. The dental hygienic device for independent use by a dog of claim 3, wherein the at least one releasably-attachable removable portion is a flared-end of the dog-bone.

5. The dental hygienic device for independent use by a dog of claim 1, wherein the device is at least part of a dog toy.

\* \* \* \* \*